US006740335B1

(12) United States Patent
Moynihan et al.

(10) Patent No.: US 6,740,335 B1
(45) Date of Patent: May 25, 2004

(54) LIPOSOMAL CAMPTOTHECIN FORMULATIONS

(75) Inventors: Karen Lewis Moynihan, Redlands, CA (US); David Lloyd Emerson, Longmont, CO (US); Su-Ming Chiang, West Hills, CA (US); Ning Hu, San Gabriel, CA (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 09/486,309

(22) PCT Filed: Sep. 15, 1998

(86) PCT No.: PCT/US98/19086

§ 371 (c)(1),
(2), (4) Date: Feb. 24, 2000

(87) PCT Pub. No.: WO99/13816

PCT Pub. Date: Mar. 25, 1999

Related U.S. Application Data

(60) Provisional application No. 60/059,083, filed on Sep. 16, 1997.

(51) Int. Cl.[7] .......................... A61K 9/127; A61K 9/133
(52) U.S. Cl. .......................... 424/450; 264/4.1; 264/4.3
(58) Field of Search .......................... 424/458; 544/361, 544/41, 60; 540/599, 553, 575; 264/4.1, 4.3

(56) References Cited

U.S. PATENT DOCUMENTS

| 5,552,156 A | * | 9/1996 | Burke ........................ 424/450 |
| 5,554,382 A | * | 9/1996 | Castor ........................ 424/450 |
| 5,559,235 A | * | 9/1996 | Luzzio ........................ 544/361 |
| 5,714,163 A | * | 2/1998 | Forssen ........................ 424/450 |

OTHER PUBLICATIONS

Weiner. Drug dev. & Industrial Pharmacy 15 (10) p1523–1554, 1989.*
Haran in BBA vol. 1151 pp. 201–205, 1990.*
Cheingjiu et al., "Research on the Pharmacokinetics of Pro–camptothecin Polyphase Liposome", 8(1):4–8, Journal of the Shenyang College of Pharmacy, 1991.
Chengjiu, et al., "Research on the Pharmacology of Pro–Camptothecin Polyphase Liposome", 7(2):118–112, Journal of the Shenyang College of Pharmacy, 1990.
Chengjiu, et al., "Research on the Tissue Distribution of Pro–Camptothecin Polyphase Liposome", 7(3):189–193, Journal of Shenyang College of Pharmacy, 1990.
Jibang, et al., "Analysis of the Therapeutic Efficacy of Using a Camptothecin Suspension in Conjunction with Surgery to Treat Primary Carcinoma of the Liver", 1:9–10, Guangxi Public Health, 1980.
Jun, et al., "IV. Research on a New Dosage Form for Anticancer Drugs—Polyphase Liposomes (III)", pp. 32–57.
Junmin, et al., "Observation of the Physical Characteristics of a Liquid Crystalline Polyphase Liposomes (139)", 17(12):942–945, Acta Pharmaceutica Sinica, 1982.

(List continued on next page.)

*Primary Examiner*—Golamudi S. Kishore
(74) *Attorney, Agent, or Firm*—Cooper & Dunham LLP

(57) ABSTRACT

Liposomal encapsulated camptothecin formulations are provided. The liposomes have improved pharmacokinetics, enhanced efficacy as anti-tumor agents and provide an increased therapeutic index as compared to the free drug and topotecan. The formulations include liposomes comprising at least one phospholipid and a camptothecin or analog thereof.

80 Claims, 9 Drawing Sheets

OTHER PUBLICATIONS

Min, et al., "Research on the Cytokinetics and Molecular Pharmacology of Camptothecin Polyphase Liposome in Tumor Cells", 5(3):161–167, Journal of the Shenyang College of Pharmacy, 1988.

Qingmin, et al., "A Method for Determining the Encapsulation Ratio of Camptothecin in Polyphase Liposomes and Studies on Its Leakage Properties", 22(12):918–922, Acta Pharmaceutica Sinica, 1987.

Qingmin, et al., "Research of the Leakage Kinetics of Camptothecin Polyphase Liposome", 7(2):113–117, Journal of the Shenyang College of Pharmacy, 1990.

Qingmin, et al., "Three–Wavelength Spectrophotometric Measurement of the Content of Camptothecin in Camptothecin Polyphase Liposome", 8(1):48–51, Journal of the Shenyang College of Pharmacy, 1991.

Quingmin, et al., "Research of the Electrophoresis Properties of Particles in Camptothecin Polyphase Liposome (Code No. 139–10) Injection", 5(3):157–160, Journal of the Shenyang College of Pharmacy, 1988.

Xueqiu, et al., "II. Research on a New Dosage Form for Anticancer Drugs—Polyphase Liposomes (I)", , ,.

Xueqiu, et al., "Advances in Research on a New Dosage Form for Anticancer Drugs—Polyphase Liposome", pp. 1–15, ,.

Xueqiu, et al., "III. Research on a New Dosage Form for Anticancer Drugs—Polyphase Liposomes (II)", pp. 22–32, , Jan. 19, 1982.

Yingjie, et al., "A New Dosage Form for an Anti–Cancer Drug–Research on a Multiphase Liposome", 1:1–14, Journal of the Shenyang College of Pharmacy, 1984.

Yuqin, et al., "Use of Orthogonal Function Spectrophotometry to Measure Flourouracil in a Multiphase Liposome", 4(3):179–183, Journal of the Shenyang College of Pharmacy, 1987.

* cited by examiner

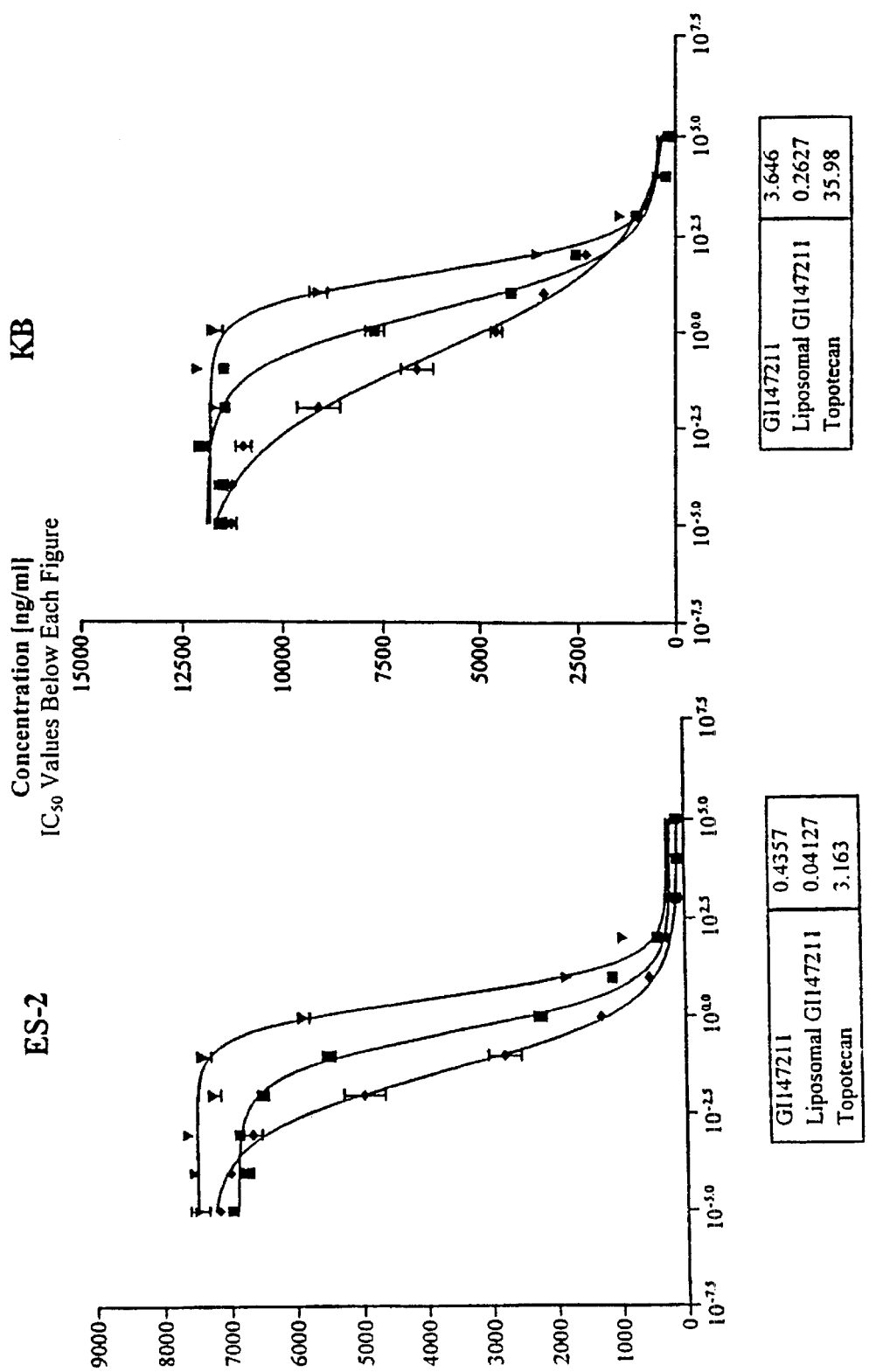

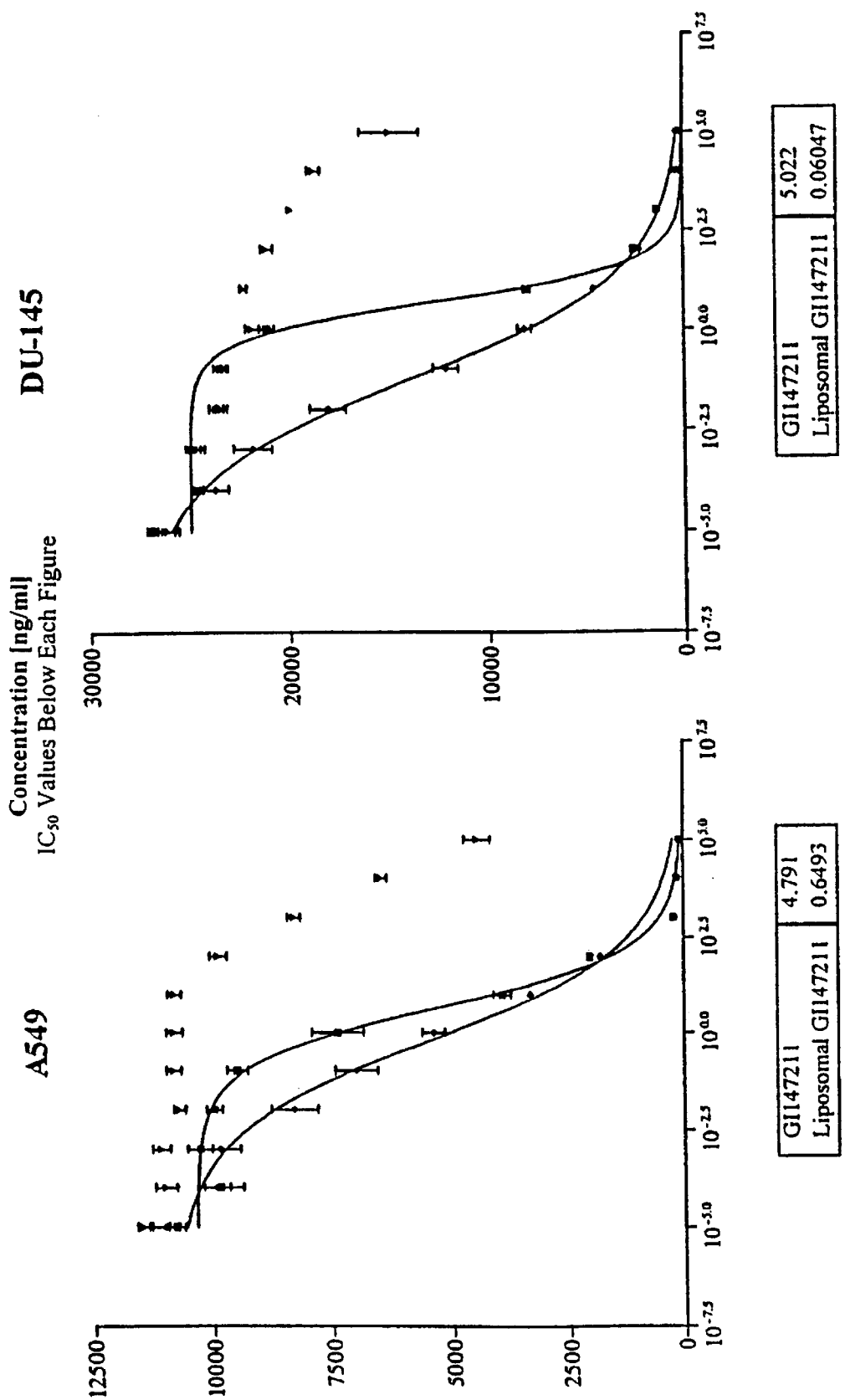

LIPOSOMAL CAMPTOTHECIN FORMULATIONS

This application is a 371 §PCT/US98/19086 filed Sep. 15, 1998 which claims priority over No. 60/059,083 filed on Sep. 16, 1997.

FIELD OF THE INVENTION

This invention relates to the fields of biochemistry and medicine, and in particular to novel liposomal formulations and process for making such formulations. More specifically, this invention relates to liposomal formulations containing camptothecin and analogs thereof. Further, this invention relates to methods of manufacturing and of using such formulations.

BACKGROUND OF THE INVENTION

Camptothecin is a pentacyclic plant alkaloid originally isolated from the bark of *Camptotheca accuminata* trees indigenous to China (Wall et al., J. Am. Chem. Soc., 94: 388 (1966)). The drug contains a fused ring structure incorporating quinoline, pyrrolidine, alpha-pyridone and a six membered lactone ring. The naturally occurring form of camptothecin is optically active, with the asymmetric carbon atom at position 20 of the lactone ring in the "S" configuration. Camptothecin and numerous analogs thereof (hereafter termed camptothecins) are currently the focus of intensive study due to the potent anti-tumor activity displayed by these compounds both in vitro and in vivo (e.g., Giovanella, et al., Science 246: 1046–1048 (1989)). The cytotoxic effects of camptothecins have also been exploited in their use as anti-viral, anti-Plasmodium and anti-haemoflagellate agents (Priel et al., U.S. Pat. No. 5,622,959; Priel et al., U.S. Pat. No. 5,422,344; Atlas, WO 9611005; Wall et al., U.S. Pat. No. 5,614,529; Shapiro et al., U.S. Pat. No. 5,496,830; Pardee, WO 9404160).

Camptothecin drugs are believed to exert their anti-tumor effect by binding to and reversibly inhibiting the action of the enzyme topoisomerase I. This enzyme is required for DNA and RNA synthesis in proliferating cells, where it catalyses the relaxation of supercoiled DNA structures that form during these processes. As a result of topoisomerase I inhibition, the biosynthesis of nucleic acids is strongly inhibited leading to DNA breakage and cell death.

Despite their impressive antitumor properties, the use of camptothecins includes a number of drawbacks. First, some camptothecins are extremely insoluble in aqueous solution, making parenteral administration of the drug problematic. Second, the lactone ring is susceptible to hydrolysis at the pH of blood plasma, resulting in a carboxylate form of the drug that has significantly reduced topoisomerase activity (Fassberg and Stella (1992) J. Pharm. Sci. 81(7):676–689; Mi et al. (1995) Biochemistry 34(42):13722–13728; Potmesil (1994) Cancer Res. 54:1431–1439; Slichenmyer et al. (1993) J. Natl. Cancer Inst. 85:271–291; Jaxel et al. (1989) Cancer Res. 49:5077–5082). Moreover, the carboxylate form is highly toxic, often inducing gastrointestinal toxicity, myelosuppression and hemorrhagic cystitis. The biologically active lactone form is also toxic.

As a result of these limitations, much effort has been invested in the synthesis of semi-synthetic camptothecin derivatives with increased water solubility, decreased toxicity and increased resistance to hydrolysis. Two examples are topotecan (Hycamtin™) (Kingsbury et al., J. Med. Chem. 34:98 (1991); Boehm et al., European Patent Application No. 321,122) which is approved for salvage therapy of metastatic ovarian carcinoma, and irinotecan (Miysaka et al., U.S. Pat. No. 4,604,463) which is approved for salvage therapy of colon cancer. Other derivatives of camptothecin and anti-tumor treatments using these derivatives are described in Wall et al. (U.S. Pat. No. 5,340,817); Wall et al. (U.S. Pat. No. 5,364,858); Wall et al. (U.S. Pat. No. 5,244,903); Wall (U.S. Pat. No. 5,180,722); Wall et al. (U.S. Pat. No. 5,227,380); Wall et al. (U.S. Pat. No. 5,049,668); Wani et al. (U.S. Pat. No. 5,122,606); Giovanella et al. (U.S. Pat. No. 5,225,404); Giovanella et al. (U.S. Pat. No. 5,552,154); Wall el al. (U.S. Pat. No. 5,401,707); Wall el al. (U.S. Pat. No. 5,122,526); Johnson et al. (WO 9311770); Johnson et al. (WO 9214471); Johnson et al. (WO 9214469); and Cherian (WO 9611669).

Recently, Luzzio et al. (U.S. Pat. No. 5,559,235) disclosed a camptothecin derivative that is moderately soluble in aqueous media, while retaining topoisomerase I activity in vitro and anti-tumor activity in vivo. This compound, 7-(4-methylpiperazinomethylene)-10,11-ethylenedioxy-20(S)-camptothecin dihydrochloride, (also known as GI147211C or lurtotecan) is less toxic overall than camptothecin, and is 5–10 times more potent than topotecan in tumor cell cytotoxicity assays (Emerson et al. (1995) Cancer Research 55:603–609). Some of the stability samples from the clinical trial formulations of GI147211C were reported to contain a sulfate-GI147211C precipitate as a result of residual levels of sulfate in glass vials (Tong et al. (1996) PDA Journal of Pharmaceutical Science and Technology 50(5):326–329). As a practical and efficient therapeutic it would be desirable to administer this compound in a manner that provides an improved therapeutic index.

Insoluble, hydrolyzable compounds may be administered in a clinical situation by packaging the compounds into lipid aggregates or constructs such as liposomes or micelles. Liposomes are known to be physiologically compatible and biodegradable delivery systems for a broad range of drugs. Furthermore, as solvation in aqueous media is not required, an insoluble compound can be delivered to the site of action in a more concentrated and easily administered medicament than the free drug alone.

Burke (U.S. Pat. No. 5,552,156) discloses liposome-associated camptothecins in which it is postulated that the lactone ring of the camptothecin intercalates with the acyl chains of the lipid bilayer. The lactone ring is effectively removed from the aqueous environment in the interior of the liposome, and protected from hydrolysis. Burke also describes how the pH of the internal liposome compartment can be lowered so that camptothecin derivatives with lower affinity for the liposome membranes can reside within the aqueous interior without undergoing hydrolysis. In vivo tests demonstrating the stability of the formulations were not performed.

Constantinides et al. (WO 95/08986) discloses formulations of camptothecin and its structurally related analogs in liposomes having at least 80% of the drug incorporated in the lipid bilayer. Pharmacokinetic studies were performed on an egg phosphatidylcholine, egg phosphatidylglycerol, camptothecin formulation. The liposomes were multilamellar and the camptothecin was passively entrapped. Increased plasma levels of camptothecin were observed over a 4-hour period after administration of the liposomal formulation as compared to those obtained with the free drug. A larger area under the plasma concentration-time curve (AUC) was obtained from liposomal versus free camptothecin, although the increase of the AUC was only about 4 fold higher.

Camptothecins incorporated within vesicles and liposomes are also described in Slater el al. (WO 9426253) and Castor et al. (WO 9615774).

SUMMARY OF THE INVENTION

The present invention provides for liposomal formulations of camptothecin and its structurally related analogs as well as methods for their preparation. The liposomes have improved pharmacokinetics, enhanced efficacy as antitumor agents, and provide an improved therapeutic index as compared to the free drug. The formulations include liposomes comprising at least one phospholipid and a camptothecin or analog thereof (referred to collectively herein as "camptothecin"). In one embodiment, the formulations include liposomes comprised of cholesterol, a phosphatidylcholine, an excipient, wherein the excipient is sulfate or citrate, and a camptothecin, wherein a portion of the camptothecin may be precipitated in the aqueous interior of the liposomes in the presence of the excipient. The preferred camptothecin for use in this invention is GI147211. Further, the formulations described herein are stable upon storage.

BRIEF DESCRIPTION OF THE FIGURES

FIGS. 3A–3D show liposomal GI147211 cytotoxicity vs. GI147211 and topotecan (TP). A) ES-2 (ovarian carcinoma), B) KB (oralpharyngial carcinoma), C) SKOV-3 (ovarian carcinoma), and D) KBV (oralpharyngial carcinoma, vincristine resistant phenotype) tumor cell proliferation by GI147211C, liposomal GI147211 and TP described by $^3$H-Thymidine Incorporation (CPM) vs. Concentration [ng/ml] values. IC$_{50}$ values (ng/ml) calculated for each data set are presented below each panel graph. ■=GI147211C, ◆=liposomal GI147211, and ▼=TP.

FIGS. 4A–4D show liposomal GI147211 cytotoxicity v. GI147211 and empty liposome A) A549 (lung carcinoma), B) DU-145 (prostate carcinoma), C) KB (oralpharyngial carcinoma), and D) LOX (melanoma) tumor cell proliferation by GI147211C, liposomal GI147211 and empty liposomes described by $^3$H-Thymidine Incorporation (CPM) vs. Concentration [ng/ml] values. IC$_{50}$ values (ng/ml) calculated for each data set are presented below each panel graph. All tumor cell types are of human derivation. ■=GI147211C, ▲=liposomal GI147211 (Lot #ALM 993-028), and ▼=Empty Liposomes.

DETAILED DESCRIPTION OF THE INVENTION

Figure 1:
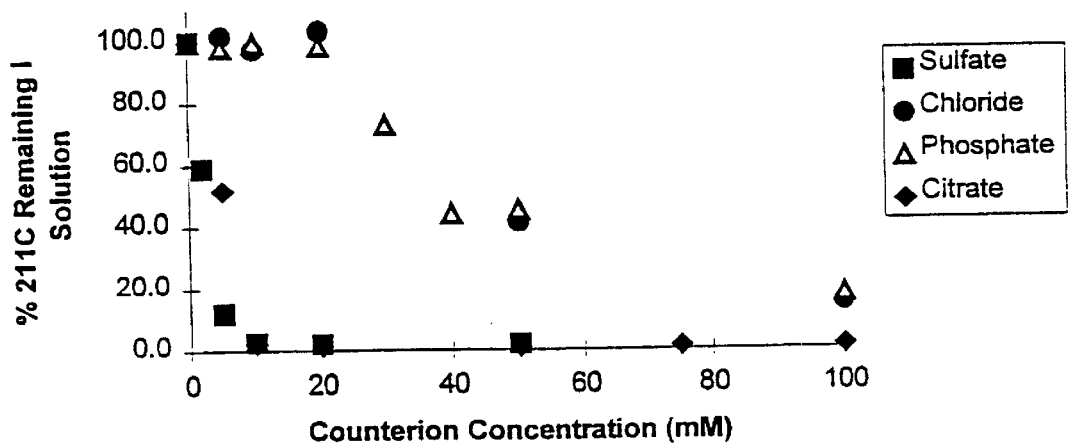
FIG. 1 depicts the precipitation of GI147211 with various counterion excipients.

Formulations comprising camptothecin encapsulated in a liposome are provided as well as methods of their preparation. The formulations have pharmaceutical uses, including as anti-tumor or anti-viral agents. In addition, the liposomes have improved pharmacokinetics, enhanced efficacy as anti-tumor agents, and provide an improved therapeutic index as compared to the free drug. The formulations include liposomes comprised of at least one phospholipid and a camptothecin. Additionally, it is also contemplated by this invention to optionally include a sterol, such as cholesterol and/or a cholesterol analog, in the liposomal formulation. In one embodiment, the formulations include liposomes comprised of cholesterol, a phosphatidylcholine, an excipient, wherein the excipient is sulfate or citrate, and a camptothecin. In one embodiment, a portion of the camptothecin may be precipitated in the aqueous interior of the liposomes by the excipient. Further, the formulations described herein are stable upon storage. In one embodiment, the liposomes are unilamellar vesicles having a size less than 200 nm, most preferably less than 100 nm, wherein the phospholipid is distearoylphosphatidylcholine (DSPC) and includes cholesterol in a 2:1 molar ratio and the camptothecin is GI147211. In the preferred embodiment, the liposomes are unilamellar vesicles having a size less than 200 nm, most preferably less than 100 nm, wherein the phospholipid is hydrogenated soy phosphatidylcholine (HSPC) and includes cholesterol in a 2:1 molar ratio and the camptothecin is GI147211. In the preferred embodiment, the lipid:camptothecin molar ratios are 5:1 to 100:1, more preferrably 10:1 to 40:1, and most preferably 15:1 to 25:1. (Lipid includes both phospholipid and cholesterol.) Furthermore, the lipsome have improved stability relative to free drug and other liposomal formulations of camptothecins.

As used herein, the term "liposome" refers to unilamellar vesicles or multilamellar vesicles such as are described in U.S. Pat. No. 4,753,788, the contents of which are incorporated herein by reference.

"Unilamellar liposomes," also referred to as "single lamellar vesicles," are spherical vesicles comprised of one lipid bilayer membrane which defines a single closed aqueous compartment. The bilayer membrane is composed of two layers of lipids; an inner layer and an outer layer (leaflet). The outer layer of the lipid molecules are oriented with their hydrophilic head portions toward the external aqueous environment and their hydrophobic tails pointed downward toward the interior of the liposome. The inner layer of the lipid lays directly beneath the outer layer, the lipids are oriented with their heads facing the aqueous interior of the liposome and their tails toward the tails of the outer layer of lipid.

"Multilamellar liposomes." also referred to as "multilamellar vesicles" or "multiple lamellar vesicles," are composed of more than one lipid bilayer membrane, which membranes define more than one closed aqueous compartment. The membranes are concentrically arranged so that the different membranes are separated by aqueous compartments, much like an onion.

The terms "encapsulation" and "entrapped," as used herein, refer to the incorporation or association of the camptothecin in or with a liposome. The camptothecin may be associated with the lipid bilayer or present in the aqueous interior of the liposome, or both. In one embodiment, a portion of the encapsulated camptothecin takes the form of a precipitated salt in the interior of the liposome. The drug may also self precipitate in the interior of the liposome.

The terms "excipient," "counterion" and "counterion excipient," as used herein, refer to a substance that can initiate or facilitate drug loading and may also initiate or facilitate precipitation of the camptothecin in the aqueous interior of the liposome. Examples of excipients include, but are not limited to, the acid, sodium or ammonium forms of monovalent anions such as chloride, acetate, lactobionate and formate; divalent anions such as aspartate, succinate and sulfate; and trivalent ions such as citrate and phosphate. Preferred excipients are citrate and sulfate.

The term "Camptothecin" refers to camptothecin and any and all related analogs or derivatives thereof which exhibit anti-tumor activity. Camptothecin drugs generally have the same core ring system. Various modifications or substitutions are found in many camptothecins, preferably such modifications or substitutions are seen in rings A and B. The camptothecin drugs generally have a similar structure that can exist as lactone and carboxylate forms as shown below. As used herein, camptothecin refers to both the lactone and carboxylate forms.

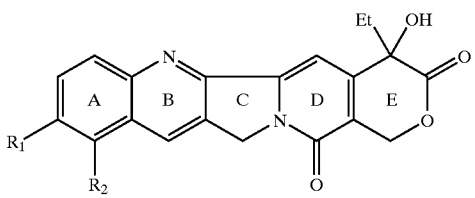

Lactone Form

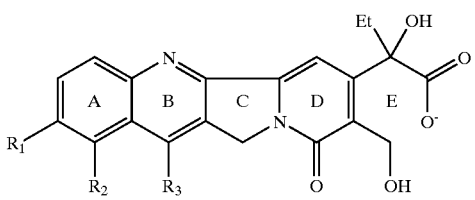

Carboxylate Form

Several examples of camptothecin drugs are provided in Table 1.

Other camptothecin drugs have the following structure:

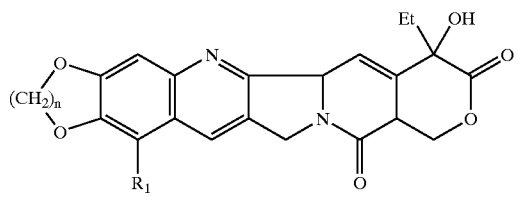

n may be 1–4. Where $R_1$ is Cl, the drug is 9-chloro-10,11-methylenedioxycamptothecin; when $R_1$ is $NH_2$, the drug is 9-amino-10,11-methylenedioxycamptothecin; and when $R_1$ is H, the drug is 10,11-methylenedioxycamptothecin.

Cmptothecin GI147211C, (7-(4-methylpiperazinomethylene)-10,11-ethylenedioxy-20(S)-camptothecin dihydrochloride) has the following structure

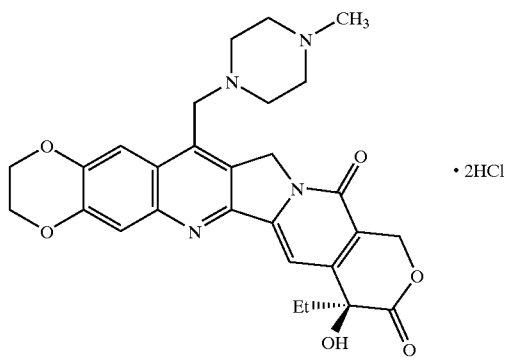

The suffix "C" in GI147211C refers to the dihydrochloride salt, and the suffix "X" in GI147211X refers to the free base.

The camptothecins may have either "A" and/or "B" ring substitutions. The preferred camptothecins include 7-(4-methylpiperazinomethylene)-10,11-ethylenedioxy-20(S)-camptothecin (GI147211), topotecan, and irinotecan (see Table 1), with the most preferred camptothecin drug being GI147211. Other camptothecins include, but are not limited to, 9-hydroxycamptothecin, 10-aminocamptothecin, 9-hydroxy-10-dimethylaminomethyl camptothecin, 20-(RS)-10,11 methylendioxycamptothecin, 9-chloro-10,11-methylenedioxy-(20S)-camptothecin, 7-ethyl-10-hydroxycamptothecin, and 7-ethyl-10-[[[4-(1-piperidino)-1-piperidino]carbonyl]-oxy]camptothecin.

"Phospholipid" refers to any one phospholipid or combination of phospholipids capable of forming liposomes. Phosphatidylcholines (PC), including those obtained from egg, soy beans or other plant sources or those that are partially or wholly synthetic, or of variable lipid chain length and unsaturation are suitable for use in the present invention. Synthetic, semisynthetic and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dipalmitoylphosphatidylcholine (DPPC) and dimyristoylphosphatidylcholine (DMPC) are suitable phosphatidylcholines for use in this invention. All of these phospholipids are commercially available. Preferred PCs are HSPC and DSPC; the most preferred is HSPC.

Further, phosphatidylglycerols (PG) and phosphatic acid (PA) are also suitable phospholipids for use in the present invention and include, but are not limited to, dimyristoylphosphatidylglycerol (DMPG), dilaurylphosphatidylglycerol (DLPG), dipalmitoylphosphatidylglycerol (DPPG), distearoylphosphatidylglycerol (DSPG) dimyristoylphosphatidic acid (DMPA), distearovlphosphatidic acid (DSPA), dilaurylphosphatidic acid (DLPA), and dipalmitoylphosphatidic acid (DPPA). Distearoylphosphatidylglycerol (DSPG) is the preferred negatively charged lipid when used in formulations. Other suitable phospholipids include phosphatidylethanolamines, phosphatidylinositols, and phosphatidic acids containing lauric, myristic, stearoyl, and palmitic acid chains. Further, incorporation of polyethylene glycol (PEG) containing phospholipids is also contemplated by the present invention.

The term "parenteral" as used herein refers to intravenous (IV), intramuscular (IM), subcutaneous (SubQ) or intraperitoneal (IP) administration.

The term "improved therapeutic index" refers to a higher therapeutic index relative to the free drug. The therapeutic index is expressed as a ratio of the lethal dose for 50% of the animals relative to the effective dose.

It is contemplated by this invention to optionally include cholesterol in the liposomal formulation. Cholesterol is known to improve liposome stability and prevent loss of phospholipid to lipoproteins in vivo.

Any lipid:camptothecin ratio that is efficacious is contemplated by this invention. Preferred lipid:camptothecin molar ratios are 5:1 to 100:1, more preferably 10:1 to 40:1. The most preferred lipid:camptothecin molar ratios are 15:1 to 25:1. Preferred liposomal formulations include phospholipid:cholesterol molar ratios over the range of 1.5:0.5 to 2:1.5. Most preferred liposomal formulation is 2:1 PC:chol with or without 1 to 4 mole percent PG. The most preferred liposomal size is less than 100 nm. The preferred loading effciency of drug is a percent encapsulated camptothecin of about 70% or greater. Encapsulation includes molecules present in the interior aqueous space of the liposome, molecules in the inner or outer leaflet of the membrane bilayer, molecules partially buried in the outer leaflet of the bilayer and partially external to the liposome, and molecules associated with the surface of the liposome, e.g., by electrostatic interactions.

Generally, the process of preparing the formulation embodied in the present invention is initiated with the preparation of a solution from which the liposomes are formed. This is done, for example, by weighing out a quantity of a phosphatidylcholine, optionally cholesterol and optionally a phosphatidylglycerol and dissolving them in an organic solvent, preferably chloroform and methanol in a 1:1 mixture (v/v) or alternatively neat chloroform. The solution is evaporated to form a solid lipid phase such as a film or a powder, for example, with a rotary evaporator, spray dryer or other means. The film or powder is then hydrated with an aqueous solution containing an excipient having a pH range from 2.0 to 7.4 to form a liposome dispersion. The preferred aqueous solution for purposes of hydration is a buffered solution of the acid, sodium or ammonium forms of citrate or sulfate. The preferred buffers are >5 mM, more preferably 50 mM, citric acid (pH 2.0–5.0), ammonium citrate (pH 2.0–5.5), or ammonium sulfate (pH 2.0 to 5.5). It would be known by one of skill in the art that other anionic acid buffers could be used, such as phosphoric acid. The lipid film or powder dispersed in buffer is heated to a temperature from about 25° C. to about 70° C. depending on the phospholipids used.

Multilamellar liposomes are formed by agitation of the dispersion, preferably through the use of a thin-film evaporator apparatus such as is described in U.S. Pat. No. 4,935,171 or through shaking or vortex mixing. Unilamellar vesicles are formed by the application of a shearing force to an aqueous dispersion of the lipid solid phase, e.g., by sonication or the use of a microfluidizing apparatus such as a homogenizer or a French press. Shearing force can also be applied using either injection, freezing and thawing, dialyzing away a detergent solution from lipids, or other known methods used to prepare liposomes. The size of the liposomes can be controlled using a variety of known techniques including the duration of shearing force. Preferably, a homogenizing apparatus is employed to form unilamellar vesicles having diameters of less than 200 nanometers at a pressure of 3,000 to 14,000 psi, preferably 10,000 to 14,000 psi and a temperature of about the aggregate transition temperature of the lipids.

Unentrapped excipient is removed from the liposome dispersion by buffer exchange to 9% sucrose using either dialysis, size exclusion column chromatography (Sephadex G-50 resin) or ultrafiltration (100,000–300,000 molecular weight cut off). Each preparation of small unilamellar liposomes is then actively loaded with GI147211 or other camptothecin, for approximately 10–30 minutes against a gradient, such as a membrane potential, generated as the external pH is titrated to the range of 5.0 to 6.5 with sodium hydroxide. The temperature ranges during the drug loading step is generally between 50–70° C. with lipid:drug ratios between 5:1 to 100:1. Unentrapped camptothecin is removed from the liposome dispersion by buffer exchange to 9% sucrose using either dialysis, size exclusion column chromatography (Sephadex G-50 resin) or ultrafiltration (100,000–300,000 molecular weight cut off). Samples are generally filtered at 55–65° C. through a 0.22 micron filter composed of either cellulose acetate or polyether sulfone.

As described above, the camptothecin is generally loaded into pre-formed liposomes using known loading procedures (see for example Deamer et al. BBA 274:323–335 (1972); Forssen U.S. Pat. No. 4,946,683; Cramer et al. BBRC 75:295–301 (1977); Bally U.S. Pat. No. 5,077,056). The loading can be by gradient or concentration loading, such as pH gradients or ammonium gradients. If a pH gradient is used, it is preferable to begin with an internal pH of approximately pH 2–3. The excipient is the counterion in the loading process and when it comes in contact with the camptothecin in the interior of the liposome, the excipient may cause a substantial portion of the camptothecin to precipitate. The drug may also self precipitate in the interior of the liposome. This precipitation may protect the lactone ring of the camptothecin from hydrolysis. An excipient, such as citrate or sulfate, may precipitate the camptothecin and can be utilized in the interior of the liposomes together with a gradient (pH or ammonia) to promote camptothecin loading.

Drug loading by pH gradient usually includes a low pH in the internal aqueous space of the liposomes, and this internal acidity is incompletely neutralized during the drug loading process. This residual internal acidity can cause chemical instability in the liposomal preparation (e.g., lipid hydrolysis), leading to limitations in shelf life. To quench this residual internal acidity, membrane permeable amines, such as ammonium salts or alkyl-amines can be added following the loading of the camptothecin in an amount sufficient to reduce the residual internal acidity to a minimum value. Ammonium salts that can be used include ones having mono-or multi-valent counterions, such as, but not limited to, anamonium sulfate, ammonium hydroxide, ammonium acetate, ammonium chloride, ammonium phosphate, ammonium citrate, ammonium succinate, ammonium lactobionate, ammonium carbonate, ammonium tartrate, and ammonium oxalate. The analogous salt of any alkyl-amine compound which is membrane permeable can also be used, including, but not limited to, methylamine, ethylamine, diethylamine, ethylenediamine, and propylamine.

The therapeutic use of liposomes can include the delivery of drugs which are normally toxic in the free form. In the liposomal form, the toxic drug may be directed away from the sensitive tissue where toxicity can result and targeted to selected areas where they can exert their therapeutic effects. Liposomes can also be used therapeutically to release drugs slowly, over a prolonged period of time, thereby reducing the frequency of drug administration through an enhanced pharmacokinetic profile. In addition, liposomes can provide a method for forming an aqueous dispersion of hydrophobic drugs for intravenous delivery.

The route of delivery of liposomes can also affect their distribution in the body. Passive delivery of liposomes involves the use of various routes of administration e.g., parenterally, although other effective administration forms, such as intraarticular injection, inhalant mists, orally active formulations, transdermal iotophoresis or suppositories are also envisioned. Each route produces differences in localization of the liposomes.

The invention also provides a method of inhibiting the growth of tumors, both drug resistant and drug sensitive, by delivering a therapeutic or effective amount of liposomal camptothecin to a tumor, preferably in a mammal. Because dosage regimens for camptothecin are well known to medical practitioners, the amount of the liposomal camptothecin formulations which is effective or therapeutic for the treatment of the above mentioned diseases or conditions in mammals and particularly in humans will be apparent to those skilled in the art. The optimal quantity and spacing of individual dosages of the formulations herein will be determined by the nature and extent of the condition being treated, the form, route and site of administration, and the particular patient being treated, and such optimums can be determined by conventional techniques. It will also be appreciated by one of skill in the art that the optimal course of treatment, i.e., the number of doses given per day for a defined number of days, can be ascertained by those skilled in the art using conventional course of treatment determination tests Inhibition of the growth of tumors associated with all cancers is contemplated by this invention, including multiple drug resistant cancer. Cancers for which the described liposomal formulations may be particularly useful in inhibiting are ovarian cancer, small cell lung cancer (SCLC), non small cell lung cancer (NSCLC), colorectal cancer, breast cancer, and head and neck cancer. In addition, it is contemplated that the formulations described and claimed herein can be used in combination with existing anticancer treatments. For example, the formulations described herein can be used in combination with taxanes such as 1) Taxol (paclitaxel) and platinum complexes for treating ovarian cancer; 2) 5FU and leucovorin or levamisole for treating colorectal cancer; and 3) cisplatin and etoposide for treating SCLC.

This invention will be more fully understood by reference to the following examples, which are intended to be illustrative of the invention, and not limiting thereof. Example 1 describes the pharmacokinetics of liposomal formulations of GI147211 prepared by three different liposome loading techniques. Example 2 describes liposomal formulations of GI147211 prepared by gradient loading and the use of ammonia to quench the liposome internal acidity. Example 3 describes precipitation of GI147211 salts. Example 4 describes the concentration dependence of precipitation of GI147211 salts using selected excipients. Example 5 describes the in vitro efficacy screening and in vivo pharmacokinetics of liposomal formulations of GI147211. Example 6 describes the in vivo antitumor efficacy of liposome encapsulated GI147211 in comparison to free drug. Example 7 describes the therapeutic index determination of GI147211, topotecan and liposomal formulations of GI147211 in two separate xenograft models. Example 8 describes repeat dose efficacy studies of liposomal formulations of GI147211 compared to free GI147211 at equally toxic doses. Example 9 compares two different liposomal preparations of GI147211 and free GI147211 in a repeat dose study in the KB tumor xenograft model.

EXAMPLE 1
Pharmacokinetics of Membrane, Passively and Actively Loaded Liposomal Formulations of GI147211

Liposomal GI147211 samples were prepared by three different loading techniques: entrapment of the drug in the liposome bilayer, passive entrapment and by active loading against a membrane potential generated by a pH gradient. The pharmacokinetics were then compared for free drug and membrane entrapped GI147211 liposomes dosed at 5 mg/kg in Sprague Dawley rats. Rats were dosed at 1 mg/kg to compare free GI147211 to passive and actively loaded liposomes.

Membrane loaded GI147211 liposomes were prepared by first cosolubilizing phospholipid (DSPC), cholesterol and GI147211 at a lipid:drug ratio of about 10:1 (w/w) in organic solvent. The solution was dried down to a thin film using nitrogen gas and elevated temperature then stored in a vacuum desiccator under reduced pressure until use. Lipid films were rehydrated with an aqueous solution, typically 9% sucrose and 10 mM sodium succinate, pH 5.4 in sufficient volume that the lipid concentration was about 50 mg/ml and the GI147211 concentration was about 5 mg/ml. Samples were then sonicated for 10–15 minutes above the aggregate lipid phase transition temperature until solutions were translucent in appearance, then filtered through a 0.22 micron filter.

Passively loaded GI147211 liposomes comprised of negative (DSPG) and/or neutrally charged lipids (DSPC) and cholesterol were prepared as follows. Aqueous solutions of GI147211C were prepared at drug concentrations of about 30 mg/ml drug by dissolving the drug in a 9% sucrose and 50 mM citric acid solution, pH 2.2 at 65° C. Lipid films or spray dried powders were prepared by cosolubilizing the lipid components in an organic solvent system, then drying the solution down to a film or powder using nitrogen gas and elevated temperature. Lipid films or powders were then hydrated at 150 mg/mL lipid to a lipid to drug ratio of 5:1 by adding the drug solutions described above, mixing and heating at about 65° C. Samples were then sonicated for about 10–15 minutes above the aggregate lipid phase transition temperature until solutions were translucent in appearance. Unentrapped GI147211 was separated from the liposome encapsulated drug using a Sephadex G-50 column eluted with 9% sucrose. The resultant liposomal GI147211 formulations were concentrated to the desired final drug concentration and the pH was adjusted to about 5.6–5.7.

Actively loaded and actively loaded/ammonia quenched samples were prepared as described in Example 2.

Particle size diameters were measured to be less than 100 nm using the MicroTrac Ultrafine Particle Analyzer for all small unilamellar vesicles described above with the exception of the membrane loaded sample which had a bimodal size distribution with 7.7% of the distribution in the main peak with a median diameter less than 100 nm.

As shown in Table 2A, when the pharmacokinetics of free drug are compared to membrane entrapped drug dosed at 5 mg/kg in rats, there is a minimal (3-fold) improvement observed in the area under the curve (AUC), maximum concentration measured at 15 minutes($C_{max}$) (2.5 fold), a two-fold decrease in the clearance rate (CL) and a one hour extension in the half life ($t_{1/2}$) for the liposomal samples. Table 2B shows the results of passively loaded liposomal GI147211 sample, prepared with and without PG, compared to free drug dosed at 1 mg/kg in rats. There is an 110–140 fold increase in AUC and $C_{max}$, 120–140 fold decrease in clearance rate, and identical half life for liposomal drug compared to free drug. Table 2B also illustrates that there is an additional order of magnitude improvement in the AUC and reduction in clearance rate in the liposomal GI147211 samples that were actively loaded against citric acid or ammonium sulfate and in one case quenched with ammonium chloride after loading compared to passive loading. 800–1200 fold increases in AUC, 200 fold increases in $C_{max}$, 600–1200 fold decreases in clearance rates, and half life extensions ranging from an additional 2 to 7 hours were observed for actively loaded GI147211 liposomes compared to free drug. This study demonstrates that the preferred loading method to achieve the best retention of drug with liposomes in vivo is active loading in the presence of a counterion which may precipitate some drug in the internal aqueous core of the liposomes.

EXAMPLE 2
Liposomal Formulations of GI147211

Phospholipids and cholesterol used herein were obtained as dry powders from Avanti Polar Lipids, Nippon, Lipoid or Sygena and were used without further purification. All other chemicals were reagent grade and were used without further purification.

For each liposome preparation described below, solutions of different counterion excipients were prepared and entrapped in the internal aqueous core of liposomes, then a water-soluble camptothecin derivative was added to the outside of the liposomes and loaded against a membrane potential generated by a pH or ion concentration difference between the inside and outside of the liposomes to enhance drug loading.

First, lipid films or spray dried powders containing various phospholipids including phosphatidylcholine, cholesterol and phosphatidylglycerol were prepared by cosolubilizing the lipid components in an organic solvent system, then drying the solution down to a film or powder using nitrogen gas and elevated temperature. Different phospholipid sources (synthetic, semi-synthetic, egg, soy), chain length (14–18 carbons) and degree of unsaturation (1 to 4 double bonds) were explored in the range of molar ratios as shown in Table 3. Each lipid powder or film was hydrated at lipid concentrations of 100–150 mg/ml with an aqueous solution containing a counterion solution for precipitation (acid, sodium or ammonium forms of citrate, sulfate, succinate, phosphate, formate, aspartate or lactobionate), in the pH range of 2.0 to 7.4. Small unilamellar liposomes (<100 nm, median diameter using the MicroTrac Ultrafine Particle Analyzer) were then formed from these mixtures at temperatures above the respective lipid phase transitions (~40–70° C.) using shear force applied with either sonication or alternatively with a homogenizer at 10,000–14,000 psi. Excipient that was not entrapped in the aqueous core of the liposomes was removed from the liposome dispersion generally by buffer exchange to 9% sucrose using dialysis, size exclusion column chromatography (Sephadex G-50 resin) or ultrafiltration (100 kD–300 kD molecular weight cut off). Each preparation of small unilamellar liposomes was then actively loaded with GI147211 for approximately 10–30 minutes against a membrane potential generated as the external pH was titrated to the range of 5.0 to 6.5 with sodium hydroxide or other suitable base. The temperature ranges during the drug loading step were generally between 50–70° C. at lipid:drug ratios between 5:1 to 100:1. Unentrapped drug was removed from the liposome dispersion by buffer exchange to 9% sucrose using dialysis, size exclusion column chromatography (Sephadex G-50 resin) or ultrafiltration using a 100 kD–300 kD molecular weight cut off membrane. Samples were filtered at 55–65° C. through a 0.22 micron filter composed of either cellulose acetate or polyether sulfone. Results of characterization are shown below in Tables 3, 4, 5 and 7.

Although this example describes liposomal preparations of GI147211, it would be known by one of skill in the art that liposomal preparations of other camptothecins can also be prepared as described.

Ammonia quench

In the formulations described above, gradient methods were used to load the camptothecin derivative GI147211C into liposomes. The setup of the gradients includes a low pH in the internal aqueous space of the liposomes, and this internal acidity may be incompletely neutralized during drug loading. Any residual internal acidity can cause chemical instability in the liposomal preparation (e.g., lipid hydrolysis), leading to limitations in shelf life. Residual internal acidity was quenched in certain liposomal formulations as follows.

410 mL of a solution containing liposomes composed of 2:1 HSPC:Cholesterol and encapsulating a 50 mM citric acid buffer at a total lipid concentration of 58.6 mg/mL, was heated to 55° C. To the liposome solution was added 60 mL of GI147211C stock solution at concentration of 20 mg/ml at a temperature of 55° C. The pH of the solution was titrated from 2.5 to about 4.4 by adding approximately 3 mL of 2.5M NaOH. The pH was then carefully titrated to 5.8 with 1 M NaOH. Following heating for approximately 20 minutes from the first base addition, the solution was then cooled to below 35° C. and ultrafiltered against 5 L of pH 6.5 dialysis solution containing 10 mM $NH_4Cl$, 9% w/w sucrose. At the end of ultrafiltration, the solution pH was adjusted to 6.5, diluted to target concentrations and filtered through a 0.2 μm pore size filter.

Liposomal GI147211 samples so treated exhibited markedly reduced rates of lipid hydrolysis, and thus are rendered more chemically stable relative to untreated samples. Generation of suitably stable liposomal samples with consistent control over lipid hydrolysis rates is required to enhance sample shelf life as a liquid. This is generally a concern for any liposome which is loaded at pH values that differ significantly from neutral, and in this case was investigated specifically in reference to liposomal GI147211 formulations.

Figure 8:
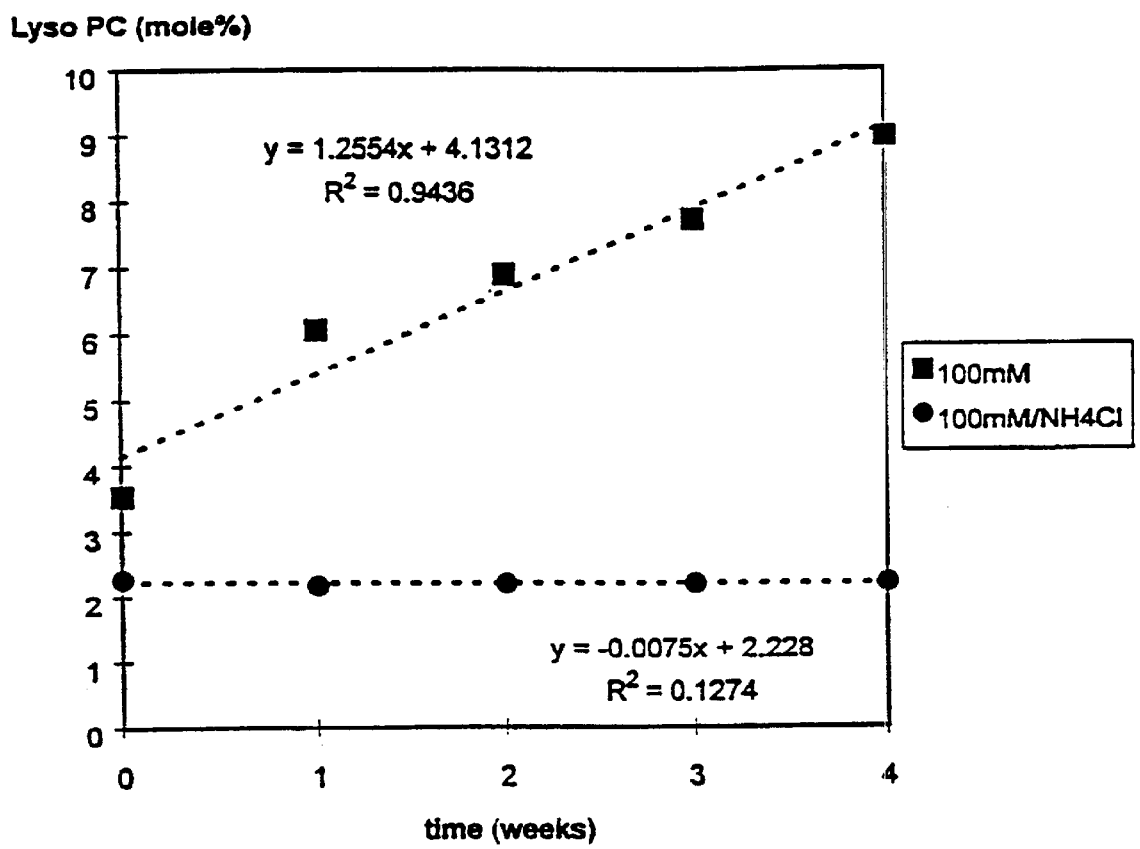
FIG. 8 shows the lipid hydrolysis rate for liposomal GI147211 (citric acid) with and without the addition of ammonium chloride to the final buffer.

FIG. 8 shows accelerated condition (25° C.) lipid hydrolysis results for a liposomal GI147211 sample prepared with 100 mM citric acid at hydration, followed by loading at a target 20:1 lipid to drug ratio. Following drug loading, the solution was split in half with a control solution and a second sample where ammonium chloride was added. The lipid hydrolysis rate for the sample with ammonium chloride added is dramatically reduced by about 167-fold in comparison to the control system.

Pharnacokinetics and efficacy studies comparing ammonium quenched versus non-quenched liposomal GI147211 samples revealed identical PK and efficacy profiles (see Table 2B and Table 15). Thus, ammonium chloride has no deleterious effect on the liposomal formulation while providing improved chemical stability for phospholipids.

EXAMPLE 3

Precipitation of GI147211 Salts

Several excipients have been identified which may induce precipitation of GI147211 from aqueous media. The excipients include, but are not limited to, the acid, sodium or ammonium forms of monovalent anions such as chloride, acetate, lactobionate and formnate; divalent anions such as succinate, aspartate and sulfate; and trivalent ions such as citrate and phosphate. To assess the relative degree of precipitation brought about with each excipient, 5 mg/ml solutions of GI147211 were prepared at low pH (2±0.5) and different counterions were added. The solutions of GI147211 and counterion were allowed to stand for 15 to 20 minutes, then centrifuiged at 3600 rpm for 10 minutes to isolate the precipitate. The quantity of GI147211 remaining in solution for each sample was then assessed by assaying the supernatants using HPLC with the following conditions: C18 ODS Hypersil column from Keystone, mobile phase of 30/70 (v/v) acetonitrile/0.1% acetic acid +0.1% aqueous triethylamine buffer, pH 3.30 with LTV detection at 270 nm. The amount of GI147211 precipitated was also tabulated by the taking the difference of the concentration of the remaining soluble fraction from Smg/ml, the original GI1147211 concentration in solution. Each number is expressed in Table 6 as percentage of the original solution concentration of 5 mg/ml. In some instances, higher counterion concentration might induce more precipitation than noted in Table 6. Sulfate, citrate, and succinate cause greater than 97% of the drug to precipitate; chloride and phosphate induce precipitation of greater than 82% of the drug; formnate and aspartate result in greater than 55% of the drug precipitated; and, sucrose and lactobionate do not cause appreciable precipitation, less than 10%, of GI147211 at the counterion concentrations tested. The precipitate will be composed of the closed lactone ring form of the camptothecin derivative as the solution pH of these experiments was approximately 2. "A" ring substituted water soluble camptothecin derivatives such as topotecan, irinotecan (CPT-11) and 9-aminocamptothecin may also display the same degree of precipitation in the presence of the counterions listed above.

EXAMPLE 4

Concentration Dependence of Precipitation of GI147211 Salts Using Selected Excipients To more fully explore the concentration dependence of GI147211 precipitation, 5 mg/ml solutions of the drug were prepared as described in Example 3 and titrated with increasing concentrations of the counterion excipients sulfate, citrate, phosphate and chloride. The solutions of GI147211 and counterion were allowed to stand for 15 to 20 minutes, then centrifuged at 3600 rpm for 10 minutes to isolate the precipitate and the supernatants were assayed as described in Example 3. FIG. 1 details the concentration dependence of the precipitation that was observed. Sulfate and citrate are the most efficient and preferred excipients for drug precipitation, reducing the fraction of drug remaining in solution at lower concentrations than chloride or phosphate with no time dependence. Liposomal samples have been prepared by active loading utilizing the counterions listed above and shown in Table 7. Percent loading of drug varied with counterion from 13% (NaCl), 61% (phosphate) to 75% and 89%, respectively for ammonium sulfate and citric acid.

In a separate study, precipitation of the camptothecin GI147211 was examined at the predicted concentration in the interior of the liposome (approx. 40 mg/ml camptothecin GI147211) after loading in the presence of 50 mM ammonium sulfate. The results show that only 0.5% of the camptothecin GI147211 remained in solution, essentially 99% of the drug had precipitated. A similar precipitation of drug is anticipated in the interior of the liposomes. Self precipitation of the drug may also be anticipated in the interior of the liposomes.

Figure 2:
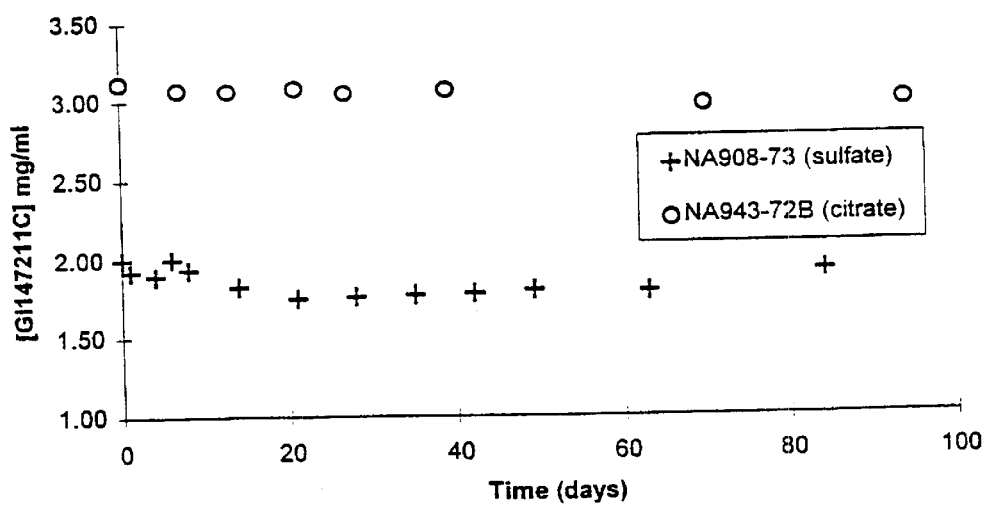
FIG. 2 depicts the stability in two representative liposomal GI147211 lots prepared for comparative efficacy.
Figures 3C, 3D:
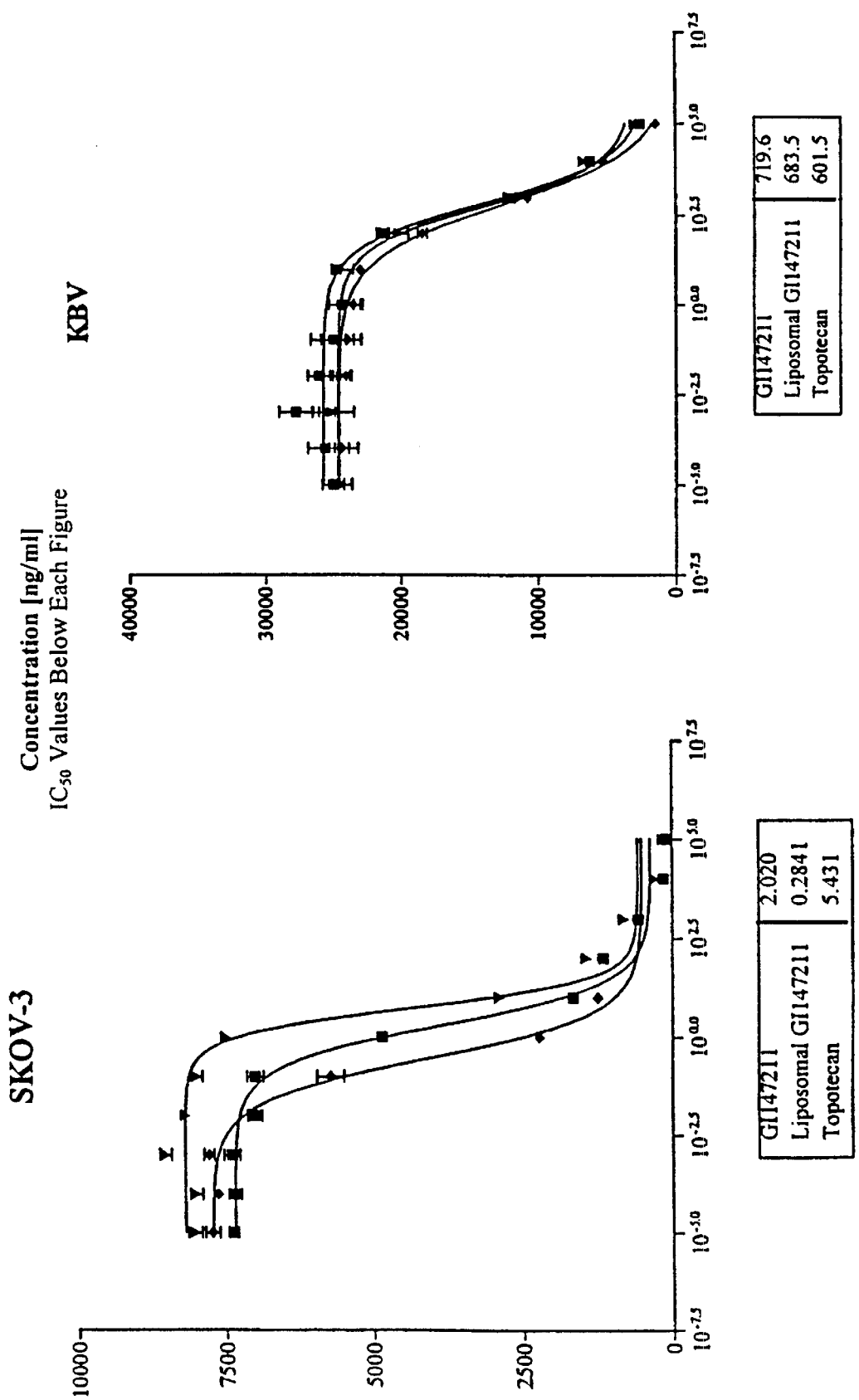
Figures 4C, 4D:
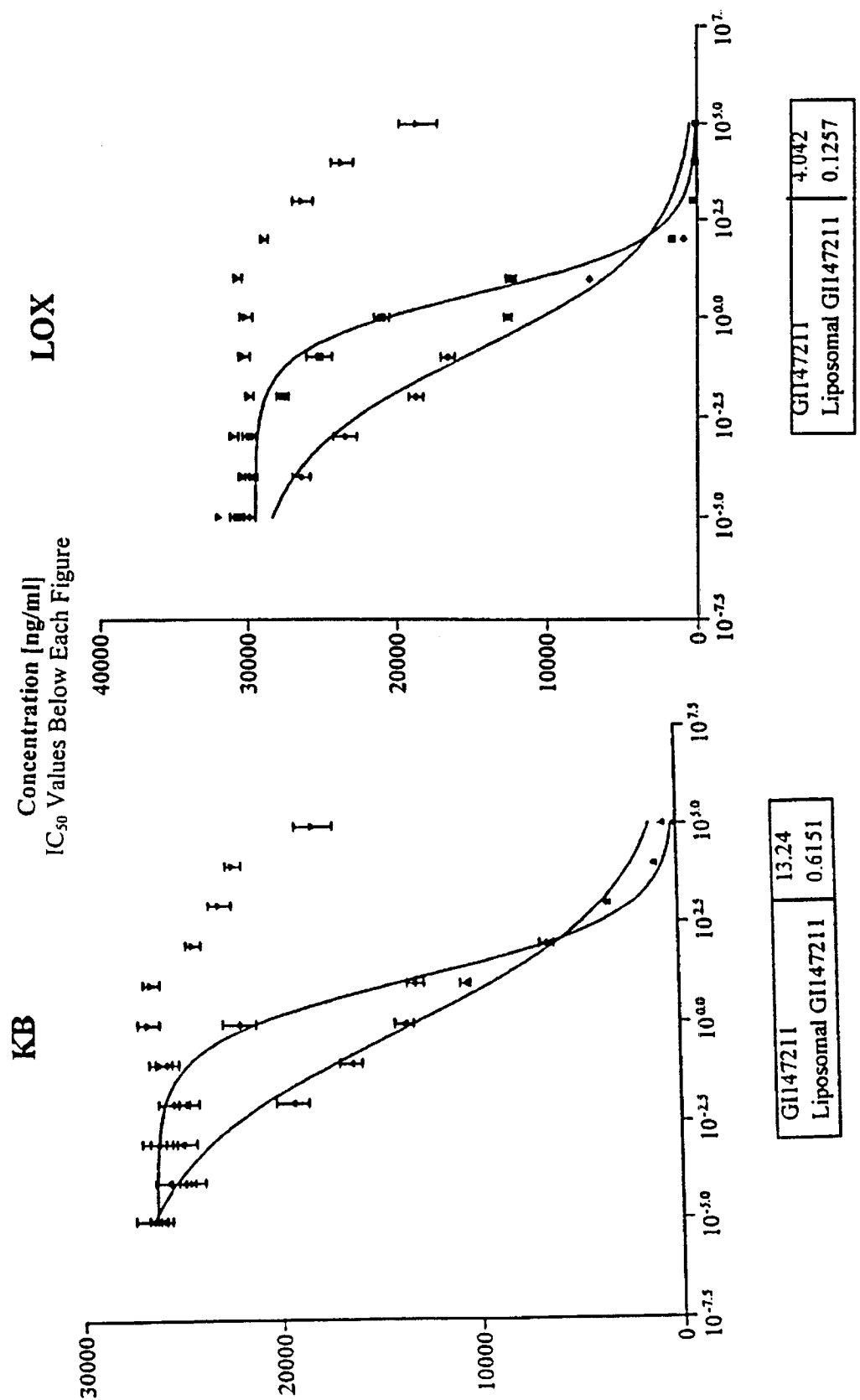

Also, shown in FIG. 2 are stability points for liposomal camptothecin GI147211 samples containing either citrate or sulfate counterions. The GI147211 losses were observed to be 4% for the sulfate or citrate sample after storage at 2–8° C. for 80–90 days, and typical precision for this type of HPLC assay is 3%.

EXAMPLE 5
In Vitro Efficacy Screening and in Vivo Pharmacokinetics of Liposomal GI147211 Formulations Liposomal formulations were prepared as described in Example 2 and samples were characterized as shown in Table 7 below and tested for in vitro efficacy screening and in vivo performance of liposomal GI147211.

In Vitro Efficacy Screening

In vitro efficacy screening has been performed using GI147211 and liposomal formulations of GI147211. The purpose of this in vitro experimentation was to ensure that liposomal encapsulation of GI147211 did not result in decreased activity relative to non-liposomal compound. Standard tumor cell-based cytotoxicity assays assessing $^3$H-thymidine incorporation were performed.

Tumor cells were seeded into 96-well tissue culture plates $(1 \times 10^4$ cells/well)=4 h prior to experimentation. Serial dilutions (1:10 dilutions, $10^5$ to $10^{-3}$ ng/ml, n=8 wells/dilution) of GI147211, liposomal GI147211 and TP treatments were prepared (immediately before use) and added to cell containing plates. Positive and negative (Tris treated) control groups were included on each assay plate. Tumor cells were then labeled with 0.25 $\mu$Ci of [methyl-$^3$H] thymidine and incubated for 42 h under tissue culture conditions (37° C., 5% $CO_2$, 100% relative humidity), except for C6, U251, A673 and B16-F1 cells which were incubated for 24 h. Cells were then lysed, harvested onto glass-fiber filters and unincorporated [methyl-$^3$H] thymidine removed by filter washing. Filters were processed for scintillation counting and cpm-$^3$H/well determined. Data (on a cell-type by cell-type basis) were normalized to control thymidine incorporation, fitted to a standard 4-parameter non-linear regression equation and $IC_{50}$ values (50% Inhibitory Concentration) determined for each treatment. Statistical differences were determined by Rank Analysis of Variance with multiple comparisons (no adjustment for multiplicity of testing) to test each cell line for differences in the $IC_{50}$ estimates between cells treated with liposomal GI147211, GI147211, and topotecan. $IC_{50}$ data are presented for each treatment group (median, minimum, and maximum) with significance indicated (p<0.05). Data are presented from multiple sets of experimentation, involving multiple liposomal formulations of GI147211.

In addition, GI147211 and liposomal GI147211 activities were also compared to that of the commercially available topoisomerase I inhibitor topotecan. The data (Table 8 and FIGS. 3A–3D) produced by this experimentation suggests that liposomal formulations of GI147211 and free GI-147211 are significantly more potent than topotecan, for the majority of tumor cell lines investigated (p<0.05, all cases). In addition, data for several tumor cell lines support the possibility that liposomal formulations of GI147211 may be more potent than GI147211 free-drug in some cases (p<0.05 as indicated in Table 8). Data presented in tabular form represent results from a large number (n>100) of cytotoxicity experiments, involving multiple lots of liposomal GI147211 produced during formulation development. Consequently, $IC_{50}$ values are presented as median values (ng/ml) with indicated maxima and minima. In addition, representative data are provided (FIGS. 4A–4D) demonstrating the consistency of tabular data with results generated using a preferred formulation. Further, data provided (FIGS. 4A–4D) indicate that drug-free empty liposome vesicles do not induce appreciable cytotoxicity, supporting the contention that observed activity of liposomal GI147211 is due to drug and not liposomal components. These data support liposomal GI147211 as an active and effective chemotherapeutic agent with the potential for increased activity relative to free GI147211.

In Vivo Pharmacokinetic Studies

Pharmacokinetic studies were carried out on various liposomal formulations of GI147211 in rats and mice by IV bolus administration. Plasma samples were precipitated with acetonitrile and the supernatant for each sample was analyzed by reverse phase HPLC using isocratic elution and monitoring fluorescence. Standards and quality control samples were analyzed in a similar manner. Concentration values were determined for unknown samples and quality control samples based on interpolation using a linear fit of the standard samples. In each study the average plasma concentration at each time point was calculated and utilized in the pharmacokinetic analysis. Noncompartmental analysis were carried out using WinNonlin™ (Standard Edition, version 1.5 ©, Scientific Consulting, Inc.) and the following parameters were calculated: the maximum concentration extrapolated at zero time (Cmax), the area under the curve from zero to infinite time (AUC total), the terminal phase half life (t½), the clearance rate (Cl), and the volume of distribution at steady state (Vss).

Table 9 summarizes the plasma pharmacokinetic parameters determined from several of these studies. In all cases the liposomal formulations show a significant increase in total exposure relative to free drug administered at a similar dose as determined by AUC total. This result was consistent in studies conducted in both rats and mice. The increase in AUC total for actively loaded liposomal formulations compared with free drug ranged from 473 to 1173-fold. The majority of the increase in exposure comes from a decrease in the volume of distribution at steady state for the liposomal formulations that approaches the plasma volume. These data support a model where the liposomal formulations reside primarily within the plasma volume and are cleared with a terminal half life of 3 to 8 hours depending on the formulation.

Dose dependence on plasma pharmacokinetics was investigated for two liposomal formulations NA-908-73 (sulfate counterion) and NA943-072B (citrate counterion). In both studies, dose dependence appeared to be linear as a function of dose as shown by similar clearance rates across the dose ranges tested for a given formulation.

Figure 5:
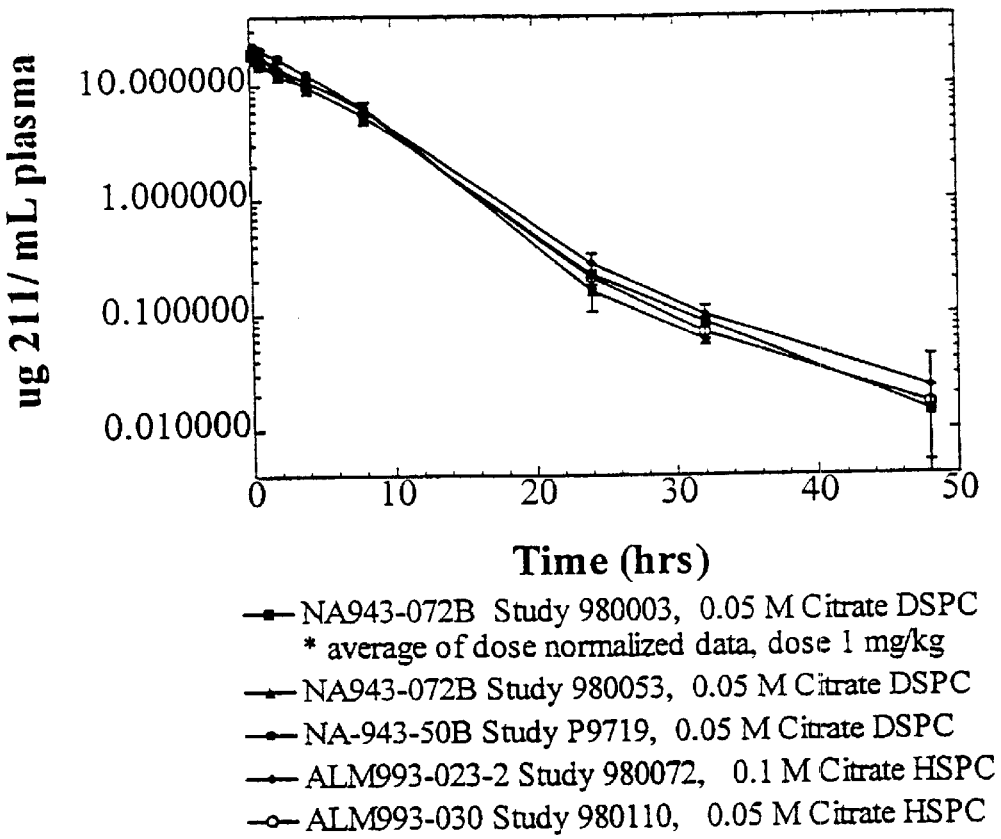
FIG. 5 is a pharmacokinetic comparison of DSPC and HSPC containing liposomal GI147211 samples performed in Sprague-Dawley rats. See Table 7 for characterization of formulations.
Figure 6:
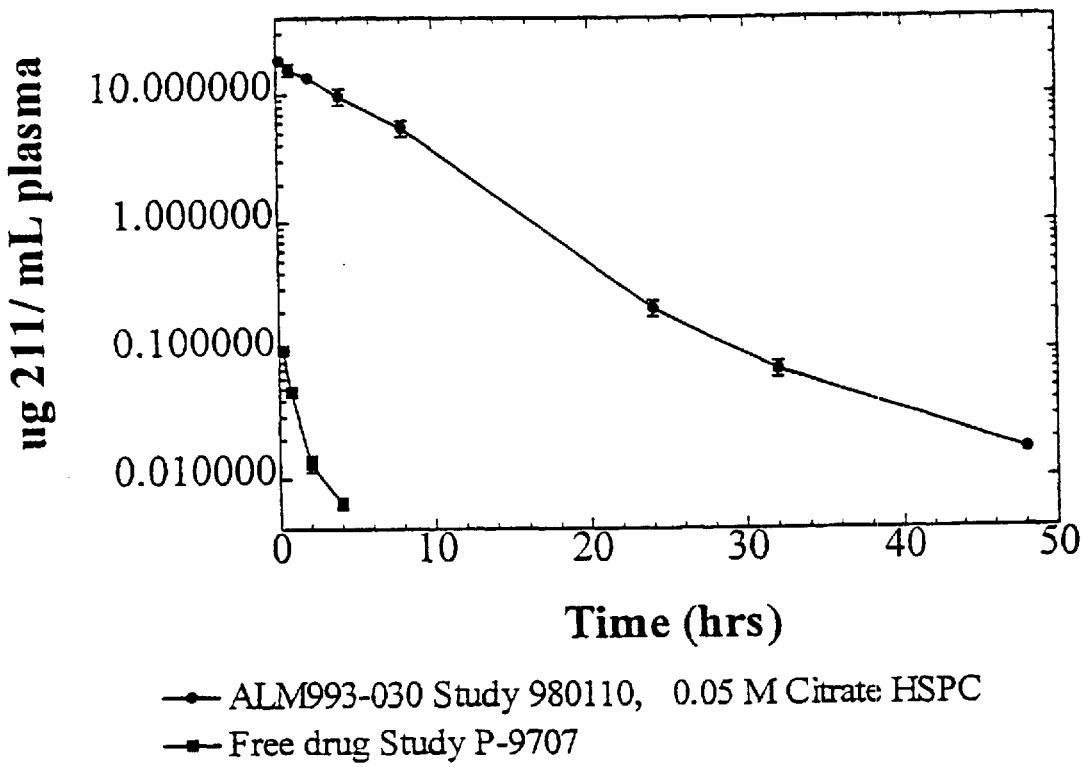
FIG. 6 is a pharmacokinetic comparison of free drug and liposomal GI147211 (ALM 993-030) performed in Sprague-Dawley rats. See Table 7 for characterization of formulation.

The citrate and sulfate formulations with either 2:1 molar ratio of HSPC or DSPC:cholesterol are preferred formulations based on increased efficacy data and pharmacokinetic properties. FIG. 5 shows the plasma concentrations as a function of time following administration in Sprague-Dawley rats, dose 1 mg/kg. Studies on one liposomal GI147211 formulation (NA943-072B), performed approximately 3 months apart, show that the pharmacokinetics does not change after liposomal drug has been stored for greater than 3 months at 2–8° C. Furthermore, citrate formulations prepared with either HSPC or DSPC show highly similar plasma pharmacokinetics. FIG. 6 shows the plasma pharmacokinetics of a formulation (2:1 HSPC:cholesterol, loaded with 50 mM citric acid and quenched with NH$_4$Cl) in comparison with free drug in Sprague-Dawley rats, dose 1 mg/kg. The AUC relative to free drug is approximately 978.

Figure 7:
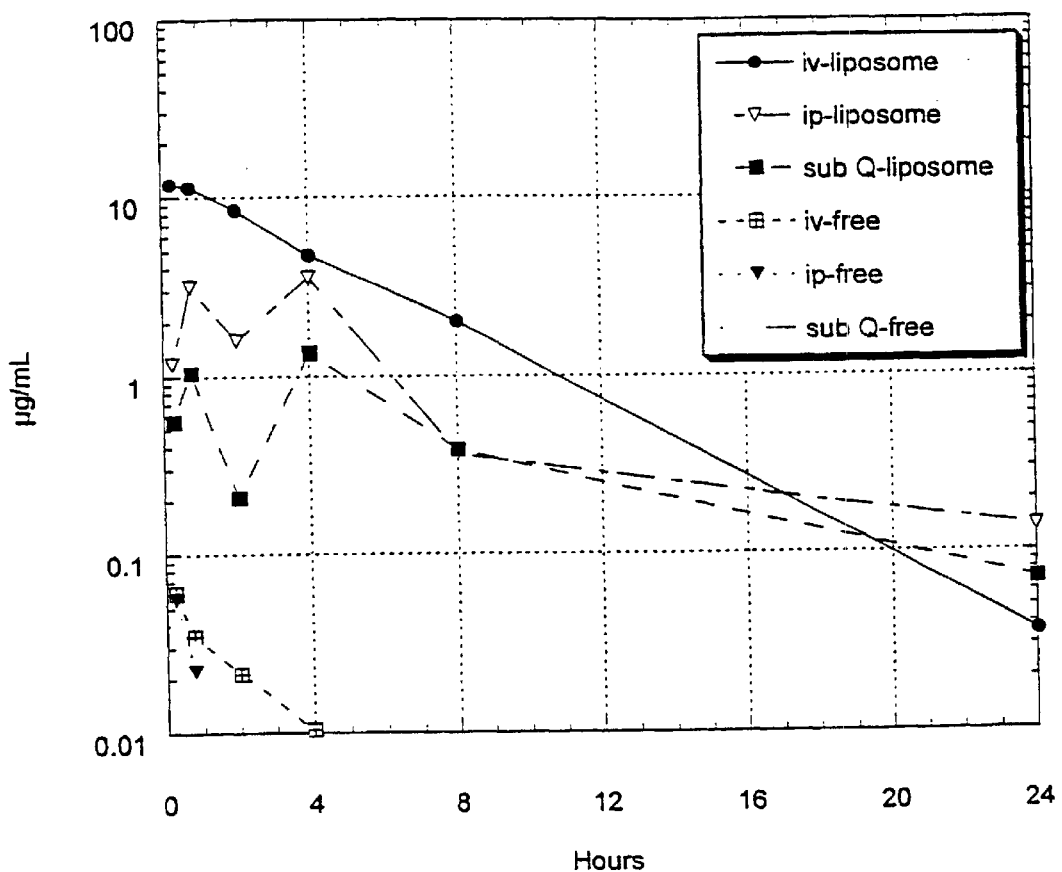
FIG. 7 is a pharmacokinetic comparison of free drug and liposomal GI147211 (1 mg/Kg) given by iv, ip, or subcutaneous routes of administration in mice (n=3, pooled data.

Routes of administration and corresponding plasma pharmacokinetics were evaluated with GI147211 free drug and liposomal formulation NA-908-73 (see Table 7 for formulation characteristics) in mice. Animals received a 1 mg/kg dose by intravenous (I.V.) intraperatoneal (I.P.) or subcutaneous administration and plasma samples were collected over 24 hours. FIG. 7 shows the plasma concentrations for free drug and liposomal GI147211 as a function of time and the plasma pharmacokinetics are summarized in Table 16. Comparison of exposure determined by AUC between free drug and liposomal showed increases of 190 to 500 fold for the three routes of delivery. This study further supports the advantage of liposomal GI147211 formulations to increase plasma circulation time and that additional routes of delivery may be utilized to maintain high concentrations in the plasma.

EXAMPLE 6
In Vivo Antitumor Efficacy of Liposome Encapsulated GI147211 vs Free GI147211

The antitumor efficacy of liposomal formulations of GI147211 was demonstrated in several human tumor xenograft models. In all the studies performed, subcutaneous tumors implanted on the anterior flank of nude mice were allowed to grow to an established size of 200+/−50 mm$^3$ prior to dosing drugs.

In vivo efficacy studies have been performed to compare the activity of the free GI147211 to the liposome formulated drug. When dosed identically, the liposomal formulation of GI147211 was shown to be more potent and efficacious in reducing tumor growth (Table 10). The xenograft models included the HT29 and SW48 human colon tumor lines, and the KB and KBV head-neck tumors. Drugs were dosed at either 6 or 9 mg/kg intravenously, on a weekly schedule for 3 consecutive weeks. In the SW48 xenograft study, the animals received a total of two cycles of therapy (6 injections), with a 10 day recovery period separating the two therapeutic courses. In the HT29 xenograft study a 12 and 14 mg/kg dose group was added. In this experiment, the liposomal GI147211 dosed animals in the high dose groups received only 2 consecutive doses of drug, while the free GI147211 groups were dosed for all three weeks. In both the KB and KBV studies, the liposomal GI147211 appeared to be more efficacious than free drug alone. This is illustrated by both the magnitude of response as well as the duration. This was particularly significant in the multiple drug resistant (MDR+) tumor line KBV, where the free drug had little effect on tumor growth, but the liposomal GI147211 demonstrated a dose dependent inhibition of tumor growth. In the two colon tumor xenograft studies, the differences were less pronounced initially, and only apparent in the SW48 tumor study after the second round of treatment. In the HT29 study the difference in tumor response was more dramatic in that the lower 6 mg/kg doses of liposomal GI147211 were as efficacious as the high dose, 14 mg/kg, free GI147211. When compared at identical dose and schedule in the SW48 and HT29 colon tumor models, liposomal GI147211 produced 95% tumor growth inhibition in both models compared to 86% and 54% produced by free drug. A more striking difference was seen in the KB tumor model where liposomal GI147211 demonstrated a Log 10 Cell Kill index of 7.13, compared to 1.64 for free drug. In addition, liposomal GI147211 produced 65% tumor growth inhibition in the MDR+tumor model KBV, whereas the free drug was essentially inactive. When dosed at equally toxic levels, liposomal GI147211 was still more efficacious than free drug alone.

EXAMPLE 7
Therapeutic Index Determination of GI147211, Topotecan and a Liposomal Formulation of GI147211 in Two Separate Xenograft Models Single dose toxicity and efficacy experiments of a liposomal formulation of GI147211, GI147211 and topotecan were performed for purposes of determining differences in therapeutic index. The established tumor xenograft models used in these studies included the KB head and neck tumor and the ES2 ovarian tumor. All test groups consisted of 10 nude mice, and the drugs were delivered as a single intravenous dose bolus injection via the tail vein. Topotecan was dosed from 6 to 40 mg/kg, GI147211 was dosed from 6–30 mg/kg, and liposomal GI147211 was dosed from 3 to 40 mg/kg. The therapeutic index was determined on day 27 post dose, by dividing the LD50 by either the ED60 or ED80. Results from both studies demonstrated that liposomal GI147211 has a consistent increase in the therapeutic index ranging from 3 to 14 fold over that of free GI147211, Table 11.

EXAMPLE 8
Repeat Dose Efficacy Studies of Liposomal GI147211 Compared to Free GI147211 at Equal Toxic Doses Several repeat dose efficacy studies comparing liposomal GI147211 to free GI147211 at equal toxic doses were performed with the KB, KBV and ES2 tumor xenograft models. Drugs were dosed on days 1,8 and 15. In all three model systems liposomal GI147211 demonstrated enhanced tumor growth delay compared to free GI147211 when dosed at equal toxic levels, Tables 12–14.

EXAMPLE 9
Comparison of HSPC vs. DSPC Based Liposomal GI147211 Preparations and Free GI147211 in a Repeat-Dose Study in the KB Tumor Xenograft Model A dose response study was performed in the KB tumor xenograft model where two different preparations of liposomal GI147211 were compared to free GI147211 following intravenous administration. On a day 1 and day 8 dose schedule and after two weeks rest the same cycle of therapy was repeated with doses delivered on day 23 and day 30. All animals in the liposomal GI147211 groups received a total of 4 drug doses, whereas the control group and the GI147211 group only received two drug doses due to excessive tumor growth. The results are shown in Table 15, and clearly demonstrate that at equal toxic doses there were no apparent differences between the two liposomal GI147211 formulations, but the GI147211 group was significantly less efficacious as an antitumor agent. The difference between the two liposomal GI147211 preparations tested was that HSPC was used in place of DSPC in batch ALM993-028 (see Table 7 for details regarding the formulations).

The invention claimed herein has been described with respect to particular exemplified embodiments. However, the foregoing description is not intended to limit the invention to the exemplified embodiments, and the skilled artisan should recognize that variations can be made within the scope and spirit of the invention as described in the foregoing specification. The invention includes all alternatives, modifications, and equivalents that may be included within the true spirit and scope of the invention as defined by the appended claims.

TABLE 1

| Camptothecin drugs | $R_1$ | $R_2$ | $R_3$ |
|---|---|---|---|
| camptothecin | H | H | H |
| 9-aminocamptothecin | H | $NH_2$ | H |
| 9-nitrocamptothecin | H | $NO_2$ | H |
| 10-hydroxycamptothecin | OH | H | H |
| Topotecan (Hycamtin ™) | OH | $CH_2NH(CH_3)_2$ | H |
| Irinotecan | [piperidinyl-piperidine carbonyl structure] | H | $CH_2CH_3$ |

TABLE 2A

Comparative Rat Pharmacokinetics Following 5 mg/kg IV dose of Free or Liposomal GI147211C

| Lot # | Lipid | Counterion | Loading | AUC ($\mu g$ * hr/ml) | $C_{max}$ (0.25 hr) ($\mu g$/ml) | $t_½$ (hr) | CL (L/kg/hr) |
|---|---|---|---|---|---|---|---|
| SMC 880-09C | — | — | free drug | 0.640 | 0.690 | 2.45 | 7.92 |
| SMC 880-13B | 2:1 DSPC:chol | 10 mM succinate | membrane | 1.980 | 1.790 | 3.50 | 3.24 |

TABLE 2B

Comparative Rat Pharmacokinetics Following 1 mg/kg IV dose of Free or Liposomal GI147211C

| Lot # | Lipid | Counterion | Loading | AUC ($\mu g$ * hr/ml) | $C_{max}$ (0.25 hr) ($\mu g$/ml) | $t_½$ (hr) | CL (L/kg/hr) |
|---|---|---|---|---|---|---|---|
| SMC 880-09C | — | — | free drug | 0.136 | 0.100 | 1.17 | 7.38 |
| SMC 880-55D | 2:1:0.1 DSPC:chol:DSPG | 50 mM citric acid | passive | 19.12 | 11.45 | 1.04 | 0.053 |
| SMC 880-56C | 2:1 DSPC:chol | 50 mM citric acid | passive | 15.79 | 9.78 | 1.11 | 0.063 |
| NA908-73 | 2:1 DSPC:chol | 50 mM ammonium sulfate | active | 106 | 19.3 | 8.44 | 0.013 |
| NA943-050B | 2:1 DSPC:chol | 50 mM citric acid | active | 159 | 22.1 | 3.2 | 0.0060 |
| ALM933-030 | 2:1 HSPC:chol | 50 mM citric acid | active $NH_4Cl$ quench | 133 | 19.6 | 4.4 | 0.0076 |

TABLE 3

Liposomal Formulations of GI147211 Loaded at 20:1 Lipid:Drug Ratio. All samples have internally entrapped counterion of 50 mM ammonium citrate, pH 4.5

| Molar Ratio | Lipid Formulation | GI147211 (mg/ml) | Median Diameter (nm) | pH | % Drug Loading |
|---|---|---|---|---|---|
| 2:0.5 | DSPC:chol | 3.2 | 77 | 6.7 | 63 |
| 2:0.75 | DSPC:chol | 4.2 | 67 | 6.8 | 83 |
| 2:1 | DSPC:chol | 4.4 | 60 | 6.9 | 89 |
| 2:1.5 | DSPC:chol | 4.4 | 67 | 6.6 | 86 |
| 1.5:0.5 | DSPC:chol | 4.2 | 71 | 6.6 | 81 |
| 2:1 | DPPC:chol | 4.3 | 49 | 6.0 | 86 |
| 2:1 | DMPC:chol | 0.9 | 40 | 5.9 | 18 |
| 2:1 | Egg PC:chol | 3.8 | 61 | 6.2 | 79 |
| 2:1 | HSPC:chol | 3.6 | 62 | 6.6 | 73 |

TABLE 4

Liposomal Formulations of GI147211 Loaded at Different Drug Lipid Ratios. All samples have internally entrapped counterion of 50 mM ammonium citrate, pH 4.5. Lipid molar ratio is 2:1 PC:cholesterol.

| Lipid Formulation | Lipid:Drug Ratio at Loading | GI147211 (mg/ml) | Median Diameter (nm) | PH | % Drug Loading |
|---|---|---|---|---|---|
| DSPC:chol | 5:1 | 10.6 | 63 | 6.7 | 53 |
| DSPC:chol | 10:1 | 8.3 | 65 | 6.4 | 85 |
| DSPC:chol | 20:1 | 4.4 | 60 | 6.9 | 89 |
| DSPC:chol | 40:1 | 2.5 | 60 | 7.0 | 91 |
| HSPC:chol | 10:1 | 6.7 | 62 | 6.6 | 61 |
| HSPC:chol | 20:1 | 3.6 | 62 | 6.6 | 73 |
| HSPC:chol | 40:1 | 1.8 | 63 | 7.1 | 70 |

TABLE 5

Percent drug loading of liposomal GI147211 as a function of encapsulated buffer pH. All samples have internally entrapped counterion of 50 mM ammonium citrate or 50 mM ammonium sulfate as indicated. Lipid molar ratio is 2:1 DSPC:cholesterol.

| Counterion | Internal pH | % Drug Loading |
|---|---|---|
| sulfate | 7.0 | 53 |
| sulfate | 6.0 | 64 |

TABLE 5-continued

Percent drug loading of liposomal GI147211 as a function of encapsulated buffer pH. All samples have internally entrapped counterion of 50 mM ammonium citrate or 50 mM ammonium sulfate as indicated. Lipid molar ratio is 2:1 DSPC:cholesterol.

| Counterion | Internal pH | % Drug Loading |
|---|---|---|
| sulfate | 4.4 | 77 |
| sulfate | 2.1 | 89 |
| citrate | 7.4 | 70 |
| citrate | 6.1 | 70 |
| citrate | 5.8 | 62 |
| citrate | 4.5 | 81 |

TABLE 6

Precipitation of GI147211 Salts

| Counterion excipient | Counterion oncentration (mM) | % GI147211 Remaining in Solution | % GI147211 Precipitated |
|---|---|---|---|
| sulfate | 20 | 2.1 | 97.9 |
| sulfate | 50 | 1.9 | 98.1 |
| citrate | 20 | 1.2 | 98.8 |
| citrate | 50 | 0.9 | 99.1 |
| succinate | 500 | 1.2 | 98.8 |
| chloride | 100 | 14.8 | 85.2 |
| phosphate | 100 | 17.7 | 82.3 |
| formate | 50 | 35.3 | 64.7 |
| aspartate | 50 | 42.2 | 57.8 |
| sucrose | 300 | 91.8 | 8.2 |
| lactobionate | 50 | 93.8 | 6.2 |

TABLE 7

Characterization of Liposomal GI147211 Samples for In Vitro, In Vivo and Pharmacokinetic Evaluations

| Lot Number | Description | GI147211 (mg/ml) | PC (mg/ml) | Cholesterol (mg/ml) | Final Lipid:Drug Ratio | Median Diameter (nm) | pH |
|---|---|---|---|---|---|---|---|
| SMC880-09C | Free drug | 3.0 | — | — | — | — | — |
| SMC880-13B | 2:1 DSPC:chol (membrane) | 5.1 | nd | nd | nd | 47* | 5.4 |
| SMC880-55D | 2:1:0.1 DSPC:chol:DSPG (passive loading) 9% sucrose/10 mM succinate | 0.5 | 31.2 | 7.6 | 84:1 | 57 | 5.7 |
| SMC880-56C | 2:1 DSPC:chol (passive loading) 9% sucrose/50 mM citric acid | 0.7 | 50.1 | 12.3 | 89:1 | 60 | 5.6 |
| SMC880-79 | 2:1 DSPC:chol 50 mM ammonium sulfate | 2.2 | 40.1 | 12.7 | 20:1 | 67 | 6.4 |
| SMC880-80 | 2:1 DSPC:chol 150 mM ammonium phosphate | 2.0 | 41.7 | 12.9 | 24:1 | 67 | 6.4 |
| SMC880-81 | 2:1 DSPC:chol 150 mM sodium chloride | 0.5 | 35.9 | 12.9 | 104:1 | 63 | 5.5 |
| SMC880-082 | 2:1 DSPC:chol 50 mM citric acid | 3.0 | 44.4 | 14.6 | 26:1 | 57 | 5.8 |
| SMC880-83 | 2:1:0.05 DSPC:chol:DSPG 50 mM citric acid | 2.5 | 37.3 | 12.7 | 20:1 | 44 | 5.6 |
| NA908-073 | 2:1 DSPC:chol 50 mM ammonium sulfate | 2.0 | 32.3 | 7.9 | 20:1 | 62 | 6.1 |
| NA943-50B | 2:1 DSPC:chol 50 mM citric acid | 3.4 | 55.9 | 14.1 | 21:1 | 58 | 6.0 |
| NA943-72B | 2:1 DSPC:chol 50 mM citric acid | 3.1 | 49.7 | 12.3 | 20:1 | 60 | 5.9 |
| SC974-021-1 | 2:1 DSPC:chol 50 mM citric acid | 2.2 | 37.4 | 8.5 | 21:1 | 60 | 6.8 |
| ALM993-023-1 | 2:1 HSPC:chol 100 mM citric acid | 2.5 | 41.7 | 10.5 | 21:1 | 70** | 4.3 |
| ALM993-023-2 | 2:1 DSPC:chol 600 mM ammonium sulfate 10 mM NH$_4$Cl quench | 3.4 | 50.2 | 12.2 | 18:1 | 43 | 6.5 |
| ALM993-028 | 2:1 HSPC:chol 50 mM citric acid 10 mM NH$_4$Cl quench | 2.5 | 37.4 | 9.5 | 19:1 | 65 | 6.5 |
| ALM993-030 | 2:1 HSPC:chol 50 mM citric acid 10 mM NH$_4$Cl quench | 2.3 | 35.6 | 8.9 | 20:1 | 64 | 6.5 | nd not determined
*77% volume in main peak
**89% volume in main peak

TABLE 8

Median IC$_{50}$ Values (ng/ml)|Range [Minimum|Maximum] and Statistical Comparisons

| Cell Line | Tumor Type | liposomal GI147211 | | | GI147211 | | | Topotecan | | |
|---|---|---|---|---|---|---|---|---|---|---|
| | | Median | Minimum | Maximum | Median | [Minimum | Maximum | Median | Minimum | Maximum |
| A549 | Lung | 8.22E−01 | 3.10E−01 | 7.40E+00 | 6.94E+00 | [2.61E+00 | 1.54E+01 | — | — | — |
| A673 | Rhabdomyo-sarcoma | 7.43E−03 | 9.05E−28 | 1.05E+01 β | 5.80E−01 | [6.00E−02 | 3.74E+00 | 6.04E+00 | 2.09E+00 | 2.16E+01 αδ |
| B16-F1 | Melanoma (murine) | 2.08E+02 | 6.44E+01 | 8.35E+02 | 1.11E+02 | [5.98E+00 | 2.42E+02 β | 3.93E+02 | 4.31E+01 | 8.95E+02 |
| BT-20 | Breast | 9.06E−04 | 1.97E−04 | 1.52E−01 δ | 8.66E−02 | [3.33E−02 | 3.23E−01 α | 3.50E+00 | — | — |
| DU-145 | Prostate | 4.42E−01 | 1.17E−02 | 1.06E+01 βδ | 1.61E+00 | [2.00E−02 | 9.07E+00 αβ | 1.35E+01 | 5.54E+00 | 1.75E+01 αδ |
| ES-2 | Ovarian | 3.00E−02 | 6.06E−05 | 7.17E−01 βδ | 4.89E−01 | [0.00E+00 | 2.14E+00 αβ | 3.89E+00 | 3.45E+00 | 4.06E+02 αδ |
| H460 | Lung, NSC | 5.90E−01 | 3.00E−02 | 4.60E+00 δ | 3.61E+00 | [1.50E−01 | 6.09E+00 α | 2.09E+01 | 2.06E+01 | 2.11E+01 φ |
| HT-29 | Colon | 1.14E−01 | 4.46E−21 | 2.23E+00 βδ | 7.63E−01 | [1.18E−02 | 3.85E+00 αβ | 4.15E+00 | 6.78E−01 | 2.76E+01 αδ |
| KB | Oralpharyngial | 3.47E+00 | 1.15E−02 | 3.05E+01 β | 4.31E+00 | [3.13E−01 | 2.75E+01 β | 3.36E+01 | 1.28E+01 | 4.19E+01 αδ |
| KBV | Oralpharyngial ξ | 4.53E+02 | 9.39E+01 | 1.24E+03 | 5.84E+02 | [2.69E+02 | 6.66E+04 | 6.11E+02 | 5.89E+02 | 6.70E+02 |
| LOX | Melanoma | 5.29E+00 | 9.82E−02 | 1.43E+01 | 1.41E+00 | [1.50E−01 | 5.33E+00 | 4.92E+00 | 3.01E+00 | 6.82E+00 φ |
| LS-513 | Cecum | 7.45E−01 | 6.84E−02 | 5.83E+00 βδ | 4.89E+00 | [1.22E+00 | 2.64E+01 αβ | 1.60E+01 | 1.15E+01 | 2.35E+01 αδ |
| MCF-7 | Breast | 7.14E+01 | 4.44E+01 | 1.90E+02 βδ | 4.41E+01 | [1.93E+01 | 8.16E+01 αβ | 2.30E+02 | 1.82E+02 | 4.89E+02 αδ |
| MDA-MB-468 | Breast | 2.85E+00 | 7.33E−01 | 8.00E+00 β | 6.42E+00 | [6.40E+01 | 1.57E+01 | 4.73E+00 | 3.57E+00 | 6.98E+01 α |
| SKOV-3 | Ovarian | 8.39E−01 | 8.37E−02 | 9.39E+00 | 1.63E+00 | [3.91E−04 | 1.90E+03 | 5.18E+00 | 1.34E−03 | 7.28E+00 |
| U251 | Glioblastoma | 3.40E+00 | 1.48E−01 | 3.39E−01 β | 3.11E+00 | [9.00E−02 | 1.13E+01 β | 1.31E+01 | 2.83E+00 | 2.22E+01 αδ |
| U87-MG | Astrocytoma | 1.88E−01 | 1.09E−24 | 3.07E+00 βδ | 2.36E+00 | [1.47E−02 | 1.79E+01 αβ | 2.16E+01 | 1.18E+01 | 1.89E+02 αδ |
| U937 | Lymphoma | 3.78E+00 | 3.14E−01 | 1.94E+01 β | 4.22E+00 | [1.70E−01 | 1.56E+01 β | 9.03E+00 | 3.49E+00 | 4.06E+01 αδ |

α = Significantly different from liposomal GI147211| p ≦ 0.05
β = Significantly different from topotecan| p ≦ 0.05
δ = Significantly different from GI147211C| p ≦ 0.05
φ = Insufficient for statistical analysis (n = 2 replicate experiments)
ξ = Vincristine Resistant Cell Line
NSC = Non-Small Cell

TABLE 9

| Drug | Study # | Formulations | Species | No. of animals | Dose (mg/kg) | AUC (total) (μg * hr/mL) | Cmax (μg/mL) | t½ (hr) | CL (L/kg/hr) | Vss (L/kg) |
|---|---|---|---|---|---|---|---|---|---|---|
| SMC-880-09C | P-9707 | free | rat | 2 | 1 | 0.136 | 0.100 | 1.17 | 7.38 | 9.23 |
| NA-908-73 | P-9710 | Ammonium sulfate DSPC | rat | 3 | 0.2 | 16.20 | 3.09 | 4.28 | 0.012 | 0.056 |
| NA-908-73 | P-9710 | Ammonium sulfate DSPC | rat | 3 | 1.0 | 80.54 | 14.66 | 8.44 | 0.013 | 0.065 |
| NA-908-73 | P-9710 | Ammonium sulfate DSPC | rat | 3 | 5 | 472.68 | 75.94 | 8.63 | 0.011 | 0.067 |
| SMC-880-09C | P-9711 | free | mice | 18 | 1 | 0.14 | 0.080 | 1.89 | 7.30 | 17.60 |
| NA-908-73 | P-9711 | Ammonium sulfate DSPC | mice | 18 | 1 | 64.81 | 12.140 | 2.77 | 0.0154 | 0.0633 |
| NS-943-50B | P-9719 | citrate 0.05 M DSPC | rat | 3 | 1 | 159.00 | 22.10 | 3.15 | 0.0060 | 0.030 |
| NA943-072B | 980003 | citrate 0.05 M DSPC | rat | 5 | 2.5 | 355.34 | 48.12 | 6.10 | 0.0072 | 0.041 |
| NA943-072B | 980003 | citrate 0.05 M DSPC | rat | 5 | 0.5 | 56.06 | 8.34 | 5.54 | 0.0091 | 0.048 |
| NA943-072B | 980003 | citrate 0.05 M DSPC | rat | 5 | 0.1 | 14.88 | 2.18 | 5.13 | 0.0068 | 0.036 |
| NA943-072B | 980003 | citrate 0.05 M DSPC | rat | 5 | 0.02 | 2.32 | 0.38 | 3.03 | 0.0086 | 0.042 |
| ALM993-023-1 | 980072 | citrate 0.1 M HSPC | rat | 3 | 1 | 147 | 19.8 | 4.9 | 0.0068 | 0.039 |
| ALM993-030 | 980110 | citrate 0.05 M HSPC | rat | 5 | 1 | 133.06 | 19.6 | 4.41 | 0.0076 | 0.040 |

TABLE 10

Efficacy Comparison of GI147211 and Liposomal GI147211 (NA908-73)**** at Identical Dose.

| Tumor | Dose Group | T-C Days | Deaths | Cures | % TGI | Day | Log 10 Cell Kill |
|---|---|---|---|---|---|---|---|
| SW48 Colon Tumor | Empty Liposome | 0 | 0//8 | 0//8 | 0 | 35 | |
| | GI147211 9 mg/kg | 40 | 1//8 | 0//8 | 86% | | 1.9 |
| | Liposomal GI147211 6 mg/kg | 63 | 0//8 | 0//8 | 92% | | 3 |
| | Liposomal GI147211 9 mg/kg | 65 | 0//4 | 0//8 | 95% | | 3.1 |
| KB Head/Neck Tumor | Empty Liposome | 0 | 2//8 | 0//8 | 0 | 22 | |
| | GI147211 6 mg/kg | 9 | 0//8 | 0//8 | 54% | | 0.87 |
| | GI147211 9 mg/kg | 17 | 0//8 | 0//8 | 73% | | 1.64 |
| | Lipsomal GI147211 6 mg/kg | 43 | 0//8 | 0//8 | 98% | | 4.14 |
| | Lipsomal GI147211 9 mg/kg | 74 | 0//8 | 1//8 | 99% | | 7.13 |

TABLE 10-continued

Efficacy Comparison of GI147211 and Liposomal GI147211 (NA908-73)**** at Identical Dose.

| Tumor | Dose Group | T-C Days | Deaths | Cures | % TGI | Day | Log 10 Cell Kill |
|---|---|---|---|---|---|---|---|
| KBV Head/Neck Tumor MDR + | Empty Liposome | 0 | 0//8 | 0//8 | 0 | 18 | |
| | GI147211 9 mg/kg | 2 | 0//8 | 0//8 | 11% | | 0.125 |
| | Liposomal GI147211 6 mg/kg | 14.5 | 1//8*** | 0//8 | 54% | | 0.906 |
| | Liposomal GI147211 9 mg/kg | 28.5 | 2//8** | 0//8 | 65% | | 1.78 |
| HT29 Colon Tumor | Empty Liposome | 0 | 0//8 | 0//8 | 0 | 26 | |
| | GI147211 6 mg/kg | 12 | 0//8 | 0//8 | 48% | | 0.753 |
| | GI147211 9 mg/kg | 12 | 0//8 | 0//8 | 54% | | 0.753 |
| | GI147211 12 mg/kg | 13 | 0//8 | 0//8 | 70% | | 0.815 |
| | GI147211 14 mg/kg | 31 | 0//8 | 0//8 | 78% | | 1.94 |
| | Liposomal GI147211 6 mg/kg | 25 | 0//8 | 0//8 | 86% | | 1.57 |
| | Liposomal GI147211 9 mg/kg | 38 | 0//8 | 0//8 | 95% | | 2.38 |
| | Liposomal GI147211 12 mg/kg* | 24 | 3//8 | 0//8 | 92% | | 1.51 |
| | Liposomal GI147211 | 25a | 0//8 | 0//8 | 82.50% | | 1.51 |

*Liposomal GI147211 groups 12 and 14 mg/kg received two total doses of drug.
***Death due to tumor ulceration
**Deaths occurred on day 6, possibly drug toxicity related
****See Table 7 for formulation
Dose Schedule QD7 × 3; iv.
SW48 Study, First dose given ip.
T-C = time difference treated and control groups to reach 1,000% Tumor Volume
% Tumor Growth Inhibition (% TGI) = 100(1-Wt/Wc); Wt and Wc mean tumor volume of treated and control group
Log 10 Cell Kill = T-C/3.32 (Td); Td = tumor doubling time
a, Starting tumor size was twice that of all other groups

TABLE 11

Comparison of Therapeutic Index

| Drug | KB Tumor (LD50/ED60) | ES2 Tumor (LD50/ED80) |
|---|---|---|
| Topotecan | 0.5 | ND* |
| GI147211 | 1 | 1.1 |
| Liposomal GI147211 (NA943-50B)** | 2.9 | 14.4 |

*ED 80 value never reached
**See Table 7 for formulation and characterization information

TABLE 12

Comparison of Antitumor Efficacy of Topotecan, GI147211 and Liposomal GI147211 (NA943-50B)* in The ES2 Tumor Xenograft Model.

| Drug and Dose | Maximum Body Weight loss | Toxic Deaths | Cures | T - C | Log Cell Kill |
|---|---|---|---|---|---|
| Topotecan, 16 mg/kg | 16% | 3 | 0 | 7.4 | 0.58 |
| GI147211, 14 mg/kg | 9% | 3 | 1 | 27 | 2.14 |
| Liposomal GI147211, 9 mg/kg | 19% | 0 | 3 | 51.4 | 4.08 |

T - C = Difference in days between treated and control groups to reach 400% tumor volume increase.
Log Cell Kill = T - C/ (3.32) (Td); where Td = Tumor doubling time in days
*See Table 7 for formulation and characterization information

TABLE 13

Anti-Tumor Efficacy of Liposomal GI147211 (NA943-50B)* vs. GI147211 at Equal Toxic Doses in The MDR +, KBV Xenograft Model

| Treatment Group | T - C | Toxic Deaths | $Log_{10}$ Cell Kill | Days to 1000% |
|---|---|---|---|---|
| Empty Liposome Control | NA | 0 | 0 | 8.57 |
| GI147211, 12 mg/kg | 7.58 | 3 | 0.53 | 16.15 |
| GI147211, 14 mg/kg | 8.43 | 3 | 0.59 | 17 |
| GI147211, 16 mg/kg | 8.43 | 1 | 0.59 | 17 |
| Liposomal GI147211, 4 mg/kg | 8.43 | 2 | 0.59 | 17 |
| Liposomal GI147211, 6 mg/kg | 15.15 | 0 | 1.06 | 23.23 |
| Liposomal GI147211, 9 mg/kg | 23.23 | 4 | 1.63 | 23.72 |

*See Table 7 for formulation and characterization information

TABLE 14

Repeat Dose Anti-Tumor Efficacy of GI147211 vs Liposomal GI147211 (NA943-50B)* KB Tumor Xenograft Model

| Drug and Dose | Mean Tumor Volume +/- (SD) | Toxic Deaths | % TGI |
|---|---|---|---|
| Empty Liposome | 1655 (618) | 0/8 | 0 |
| GI147211 in D5W, 14 mg/kg | 275 (67) | 0/8 | 83 |
| GI147211 in empty liposomes, 14 mg/kg | 278 (61) | 0/8 | 83 |
| Liposomal GI147211 9 mg/kg | 91 (38) | 0/8 | 95 |

TABLE 14-continued

Repeat Dose Anti-Tumor Efficacy of GI147211 vs Liposomal GI147211 (NA943-50B)* KB Tumor Xenograft Model

| Drug and Dose | Mean Tumor Volume +/− (SD) | Toxic Deaths | % TGI |
|---|---|---|---|
| Liposomal GI147211 6 mg/kg | 114 (77) | 1/8 | 93 |

% TGI = 100 (1-Wt/Wc); where Wt is the mean tumor volume of the treated group at day 15 and Wc is the mean tumor volume of the control group at day 15.
*See Table 7 for formulation and characterization information.

TABLE 15

Comparison of HSPC (ALM 993-028) vs. DSPC (SC 974-021-1) Liposomal GI147211 Formulations and GI147211 in the KB Xenograft Model.

| Drug/Dose | T − C | Toxic Deaths | Cures | % TGI | Log Cell Kill Index |
|---|---|---|---|---|---|
| D5W control | 0 | 0/8 | 0/8 | 0% | 0 |
| GI147211, 14 mg/kg | 13.4 | 0/8 | 0/8 | 77.5% | 0.81 |
| Liposomal GI147211 | | | | | |
| SC974-021-1; 3 mg/kg | 40.2 | 0/8 | 1/8 | 92.9% | 2.42 |
| SC974-021-1; 6 mg/kg | 45.8 | 0/8 | 2/8 | 96.2% | 2.75 |
| SC974-021-1; 9 mg/kg | 73 | 0/8 | 1/8 | 98.1% | 4.39 |
| ALM993-028; 3 mg/kg | 35 | 0/8 | 0/8 | 91% | 2.37 |
| ALM993-028; 6 mg/kg | 45.8 | 0/8 | 1/8 | 94.6% | 2.75 |
| ALM993-028; 9 mg/kg | 53.4 | 1/8 | 1/8 | 96.6% | 3.21 |

T − C = Time difference between treated and control groups to achieve 400% tumor volume increase.
% Tumor Growth Inhibition (% TGI) = 100(1-Wt/Wc); Wt and Wc represent mean tumor volume of treated and control groups at day 18.
Log cell Kill Index = T − C/3.32(Td); Td = Tumor doubling time.
Cure refers to tumor-free animals at day 60.

dilaurylphosphatidylglycerol, dipalmitoylphosphatidylglycerol, distearoylphosphatidylglycerol.

5. The liposome of claim 4 wherein said phosphatidylglycerol is distearoylphosphatidylglycerol.

6. The liposome of claim 1 further comprising a counterion.

7. The liposome of claim 6 wherein said counterion is an acid, a sodium or an ammonium form of a monovalent anion, a divalent anion or trivalent anion.

8. The liposome of claim 7 wherein said monovalent anion is chloride, acetate, lactobionate or formate; said divalent anion is aspartate, succinate or sulfate; and said trivalent anion is citrate or phosphate.

9. The liposome of claim 1 wherein the phosphatidylcholine to cholesterol molar ratio is about 2:1.

10. The liposome of claim 9 wherein said liposome is unilamellar and less than 100 nm in diameter.

11. The liposome of claim 1 wherein the phosohatidylcholine and cholesterol constitute the lipid part of the liposome, said lipid to 7-(4-methylpiperazinomethylene)-10,11-ethylenedioxy-20(S)-camptothecin molar ratio is from about 5:1 to 100:1.

12. The liposome of claim 11 wherein said lipid to 7-(4-methylipiperazinomethylene)-10,11-ethylenedioxy-20 (S)-camptothecin molar ratio is from about 5:1 to 40:1.

13. The liposome of claim 12 wherein said lipid to 7-(4-methylpiperazinomethylene)-10,11-ethylenedioxy-20 (S)-camptothecin molar ratio is about 20:1.

14. The liposome of claim 2, wherein the hydrogenated soy phosphatidylcholine to cholesterol molar ratio is about 2:1.

15. The liposome of claim 14 wherein said liposome is unilamellar and less than 100 nm in diameter.

16. The liposome of claim 15 wherein the hydrogenated soy phosphatidylcholine and cholesterol constitute the lipid part of the liposome, said lipid to 7-(4-methylpiperazinomethylene)-10,11-ethylenedioxy-20 (S)-camptothecin molar ratio is from about 5:1 to 100:1.

TABLE 16

Routes of Administration in Mice

| Drug | Study # | Formulations | Species | No. of animals | Drug | Dose (mg/kg) | Dosing route | AUC (total) (μg * hr/mL) | Cmax (μg/mL) | Tmax (hr) | CL (L/kg/hr) | Vss (L/kg) |
|---|---|---|---|---|---|---|---|---|---|---|---|---|
| SMC-880-09C | P-9711 | | mice | 18 | free | 1 | I.V. | 0.14 | 0.080 | 0.00 | 7.3038 | 17.6047 |
| NA-908-73 | | Ammonium sulfate | mice | 18 | liposome | 1 | I.V. | 64.81 | 12.140 | 0.00 | 0.0154 | 0.0633 |
| SMC-880-09C | | | mice | 18 | free | 1 | I.P. | 0.047 | 0.056 | 0.25 | N/A | N/A |
| NA-908-73 | | Ammonium sulfate | mice | 18 | liposome | 1 | I.P. | 23.43 | 3.558 | 4.00 | N/A | N/A |
| SMC-880-09C | | | mice | 18 | free | 1 | Sub. Q | 0.055 | 0.042 | 0.25 | N/A | N/A |
| NA-908-73 | | Ammonium sulfate | mice | 18 | liposome | 1 | Sub. Q | 10.569 | 1.349 | 4.00 | N/A | N/A |

We claim:

1. A liposome comprising cholesterol, at least one phosphatidylcholine selected from the group consisting of distearoylohosphatidylcholine and hydrogenated soy phosohatidylcholine, and 7-(4-methylpiperazinomethylene)-10,11-ethylenedioxy-20(S)-camptothecin, wherein the phosphatidylcholine to cholesterol molar ratio is from about 1.5:0.5 to 2:1.5.

2. The liposome of claim 1 wherein said phosphatidylcholine is hydrogenated soy phosphatidylcholine.

3. The liposome of claim 1 wherein said liposome further comprises phosphatidylglycerol.

4. The liposome of claim 3 wherein said phosphatidylglycerol is selected from the group consisting of dimyristoylphosphatidylglycerol, 17. The liposome of claim 16 wherein said lipid to 7-(4-methylpiperazinomethylene)-10,11-ethylenedioxy-20 (S)-camptothecin molar ratio is from about 5:1 to 40:1.

18. The liposome of claim 17 wherein said lipid to 7-(4-methylpiperazinomethylene)-10,11-ethylenedioxy-20 (S)-comptothecin molar ratio is 20:1.

19. The liposome of claim 18 further comprising a counterion.

20. The liposome of claim 19 wherein said counterion is an acid, a sodium or an ammonium form of a monovalent anion, a divalent anion or trivalent anion.

21. The liposome of claim 20 wherein said monovalent anion is chloride, acetate, lactobionate or formate; said divalent anion is aspartate, succinate or sulfate; and said trivalent anion is citrate or phosphate.

22. The liposome of claim 21 wherein said counterion is citrate.

23. A process for producing the liposome of claim 1 comprising:
   a) forming a lipid film or powder comprised of phosphatidylcholine and cholesterol;
   b) hydrating said lipid film or powder with an aqueous buffer containing a counterion solution;
   c) applying a shearing force whereby liposomes that are unilamellar and less than 100 nm are obtained in aqueous medium;
   d) adding 7-(4-methylpiperazinomethylene)-10,11-ethylenedioxy-20(S)-camotothecin to the aqueous medium; and
   e) generating a gradient between the aqueous medium inside the liposome and the aqueous medium external to the liposome whereby the gradient causes the 7-(4-methylpiperazinomethylene)-10,11-ethylenedioxy-20(S)-camotothecin to load into the liposome.

24. The process of claim 23 wherein the gradient is a pH gradient.

25. The process of claim 23 wherein the phosphatidylcholine to cholesterol molar ratio is from about 1.5:0.5 to 2:1.5.

26. A method of inhibiting the growth of a tumor comprising the administration of a therapeutic or effective amount of the liposome of claim 1 to the tumor.

27. The method of claim 26 wherein said tumor is drug resistant or drug sensitive.

28. The method of claim 27 wherein said tumor is from a cancer selected from the group consisting of ovarian small cell lung cancer, non-small cell lung cancer, colorectal cancer, breast cancer, and head and neck cancer.

29. A liposome encapsulating 7-(4-methylpiperazinomethylene)-10,11-ethylenedioxy-20(S)-camptothecin, wherein said liposome is comprised of the lipids hydrogenated soy phosphatidylcholine (HSPC) and cholesterol and wherein HSPC:cholesterol are in a molar ratio of about 2:1, and wherein the lipids:camptothecin molar ratio is from 10:1 to 40:1, and wherein said liposome is unilamellar and less than 100 nm in diameter.

30. A process for producing a liposome of claim 29 comprising
   a) forming a lipid film or powder comprised of hydrogenated soy phosphatidylcholine and cholesterol in a molar ratio of about 2:1;
   b) hydrating said lipid film or powder with an aqueous buffer containing a counterion solution;
   c) applying a shearing force whereby liposomes that are unilamellar having an average size of less than 100 nm are obtained in aqueous medium;
   d) adding 7-(4-methylpiperazinomethylene)-10,11-ethylenedioxy-20(S)-camptothecin to the aqueous medium in an amount which results in a lipid:camotothecin molar ratio from 10:1 to 40:1; and
   e) generating a gradient between the aqueous medium inside the liposome and the aqueous medium external to the liposome whereby the gradient causes the 7-(4-methylpiperazinomethylene)-10,11-ethylenedioxy-20(S)-camptothecin to load into the liposome.

31. The process of claim 30 wherein the gradient is a pH gradient.

32. A method of inhibiting the growth of a tumor comprising the administration of a therapeutic or effective amount of the liposome of claim 29 to the tumor.

33. The method of claim 32 wherein said tumor is drug resistant or drug sensitive.

34. The method of claim 33 wherein said tumor is from a cancer selected from the group consisting of ovarian, small cell lung cancer, non-small cell lung cancer, colorectal cancer, breast cancer, and head and neck cancer.

35. A process for making liposomes comprising 7-(4-methylpiperazinomethylene)-10,11-ethylenedioxy-20(S)-camotothecin, said process comprising:
   a) forming a lipid film or powder comprised of hydrogenated soy phosphatidylcholine and cholesterol;
   b) hydrating said lipid film or powder with an aqueous buffer containing a counterion solution;
   c) applying a shearing force whereby liposomes that are unilamellar and less than 100 nm are obtained in aqueous medium;
   d) adding 7-(4-methylpiperazinomethylene)-10,11-ethylenedioxy-20(S)-camptothecin to the aqueous medium; and
   e) generating a gradient between the aqueous medium inside the liposome and the aqueous medium external to the liposome whereby the gradient causes the 7-(4-methylpiperazinomethylene)-10,11-ethylenedioxy-20(S)-camotothecin to load into the liposome.

36. The process of claim 35 wherein the hydrogenated soy phosphatidylcholine to cholesterol molar ratio is from about 1.5:0.5 to 2:1.5.

37. The process of claim 35 wherein the gradient is a pH gradient.

38. The process of claim 37 wherein the pH of the aqueous medium inside the liposome relative to the aqueous medium external to the liposome is less.

39. The process of claim 37 further comprising increasing the pH of the aqueous medium inside of the liposome by adding a membrane permeable amine to the aqueous medium external to the liposome.

40. The process of claim 39 wherein said membrane permeable amine is selected from the group consisting of an ammonium salt and an alkyl-amine.

41. The process of claim 40 wherein said ammonium salt has a mono- or multivalent counterion.

42. The process of claim 41 wherein said ammonium salt is selected from the group consisting of ammonium sulfate, ammonium hydroxide, ammonium acetate, ammonium chloride, ammonium phosphate, ammonium citrate, ammonium succinate, ammonium lactobionate, ammonium carbonate, ammonium tartrate, and ammonium oxalate.

43. The process of claim 41 wherein said alkyl-amine is selected from the group consisting of methyl amine, ethylamine, diethylamine, ethylenediamine and propylamine.

44. The process of claim 35 wherein lipid film further comprises a phosphatidylglycerol.

45. The process of claim 44 wherein said phosphatidylglycerol is selected from the group consisting of dimyristoylphosphatidylglycerol, dilaurylphosphatidylglycerol, dipalmitoylphosphatidylglycerol, distearoylphosphatidylglycerol.

46. The process of claim 47 wherein said phosphatidylglycerol is distearoylphosphatidylglycerol.

47. The process of claim 35 wherein said hydrogenated soy phosphatidylcholine to cholesterol molar ratio is about 2:1.

48. The process of claim 35 wherein said lipid to 7-(4-methylpiperazinomethylene)-10,11-ethylenedioxy-20(S)-camptothecin molar ratio is from about 10:1 to 40:1.

49. The process of claim 48 wherein said lipid to 7-(4-methylpiperazinomethylene)-10,11-ethylenedioxy-20(S)-camptothecin molar ratio is about 20:1.

50. The process of claim 24 wherein the pH of the aqueous medium inside the liposome relative to the aqueous medium external to the liposome is less.

51. The process of claim 50 further comprising increasing the pH of the aqueous medium inside of the liposome by adding a membrane permeable amine to the aqueous medium external to the liposome.

52. The process of claim 51 wherein said membrane permeable amine is selected from the group consisting of an ammonium salt and an alkyl-amine.

53. The process of claim 52 wherein said ammonium salt has a mono- or multivalent counterion.

54. The process of claim 53 wherein said ammonium salt is selected from the group consisting of ammonium sulfate, ammonium hydroxide, ammonium acetate, ammonium chloride, ammonium phosphate, ammonium citrate, ammonium succinate, ammonium lactobionate, ammonium carbonate, ammonium tartrate, and ammonium oxalate.

55. The process of claim 52 wherein said alkyl-amine is selected from the group consisting of methylamine, ethylamine, diethylamine, ethylenediamine and propylamine.

56. The process of claim 23 wherein said phosphatidylcholine is hydrogenated soy phosphatidylcholine.

57. The process of claim 56 wherein said lipid film further comprises a phosphatidylglycerol.

58. The process of claim 57 wherein said phosphatidylglycerol is selected from the group consisting of dimyristoylphosphatidylglycerol, dilaurylphosphatidylglycerol, dipalmitoylphosphatidylglycerol, distearoylphosphatidylglycerol.

59. The process of claim 58 wherein said phosphatidylglycerol is distearoylphosphatidylglycerol.

60. The process of claim 25 wherein said phosphatidylcholine to cholesterol molar ratio is about 2:1.

61. The process of claim 23 wherein said lipid to camptothecin molar ratio is from about 10:1 to 40:1.

62. The process of claim 61 wherein said lipid to camptothecin molar ratio is about 20:1.

63. A process for making liposomes comprising 7-(4-methylpiperazinomethylene)-10,11-ethylenedioxy-20(S)-camptothecin, said process comprising:
 a) forming a lipid film or powder comprised of hydrogenated soy phosphatidylcholine and cholesterol;
 b) hydrating said lipid film or powder with an aqueous buffer containing a counterion solution;
 c) adding 7-(4-methylpiperazinomethylene)-10,11-ethylenedioxy-20(S)-camptothecin to the aqueous buffer;
 d) generating a gradient between the aqueous medium inside the liposome and the aqueous medium external to the liposome whereby the gradient causes the 7-(4-methylpiperazinomethylene)-10,11-ethylenedioxy-20(S)-camptothecin to load into said liposome; and
 e) adding a membrane permeable amine to the aqueous medium external to the liposome whereby the pH of the aqueous medium inside the liposome is decreased.

64. A liposome encapsulating 7-(4-methylpiperazinomethylene)-10,11-ethylenedioxy-20(S)-camptothecin, wherein said liposome is produced by the process comprising:
 a) forming a lipid film or powder comprised of hydrogenated soy phosphatidylcholine and cholesterol;
 b) hydrating said lipid film or powder with an aqueous buffer containing a counterion solution;
 c) adding 7-(4-methylpiperazinomethylene)-10,11-ethylenedioxy-20(S)-camptothecin to the aqueous buffer;
 d) generating a gradient between the aqueous medium inside the liposome and the aqueous medium external to the liposome whereby the gradient causes the 7-(4-methylpiperazinomethylene)-10,11-ethylenedioxy-20(S)-camptothecin to load into said liposome; and
 e) adding a membrane permeable amine to the aqueous medium external to the liposome whereby the pH of the aqueous medium inside the liposome is decreased.

65. A unilamellar liposome encapsulating 7-(4-methylpiperazinomethylene)-10,11-ethylenedioxy-20(S)-camptothecin, wherein the liposome comprises a) hydrogenated soy phosphatidylcholine or distearoylphosphatidylcholine, b) cholesterol, and c) a citrate or a sulfate as a counterion, wherein the ratio of a) to b) is about 2:1.

66. The unilamellar liposome of claim 65, further comprising ammonium chloride.

67. The unilamellar liposome of claim 65, wherein a) is hydrogenated soy phosphatidylcholine and wherein the citrate in c) is 50 mM ammonimum citrate.

68. The unilamellar liposome of claim 65, wherein a) is hydrogenated soy phosphatidylcholine and wherein the citrate in c) is 100 mM ammonium citrate.

69. The unilamellar liposome of claim 65, wherein a) is distearoylphosphatidylcholine and wherein the citrate in c) is 50 mM ammonium citrate acid.

70. The unilamellar liposome of claim 65, wherein a) is distearoylphosphatidylcholine and wherein the sulfate in c) is ammonium sulfate.

71. The unilamellar liposome of claim 67, wherein said liposome is about 62 nm in diameter.

72. The unilamellar liposome of claim 67 wherein said liposome is about 63 nm in diameter.

73. The unilamellar liposome of claim 69 wherein said liposome is about 60 nm in diameter.

74. The unilamellar liposome of claim 69 wherein said liposome is about 63 nm in diameter.

75. The unilamellar liposome of claim 69 wherein said liposome is about 65 nm in diameter.

76. A pharmaceutical composition comprising unilamellar liposomes encapsulating 7-(4-methylpiperazinomethylene)-10,11-ethylenedioxy-20(S)-camptothecin, wherein the liposomes comprise a) hydrogenated soy phosphatidylcholine or distearoylphosphatidylcholine, b) cholesterol, c) a citrate or a sulfate as a counterion, and d) a pharmaceutically acceptable carrier and wherein the ratio of a) to b) is about 2:1.

77. The pharmaceutical composition of claim 76, wherein the liposomes have a median diameter of 60 nm.

78. The pharmaceutical composition of claim 76, wherein the liposomes have a median diameter of 62 nm.

79. The pharmaceutical composition of claim 76, wherein the liposomes have a median diameter of 63 nm.

80. The pharmaceutical composition of claim 76, wherein the liposomes have a median diameter of 65 nm.

* * * * *